US009808503B2

(12) United States Patent
Spertini et al.

(10) Patent No.: US 9,808,503 B2
(45) Date of Patent: Nov. 7, 2017

(54) ALLERGEN PEPTIDE FRAGMENTS AND USE THEREOF FOR TREATMENT OF BIRCH POLLEN ALLERGIES

(71) Applicant: ANERGIS S.A., Epalinges (CH)

(72) Inventors: Francois Spertini, Epalinges (CH); Blaise Corthesy, Cugy (CH)

(73) Assignee: ANERGIS S.A., Epalinges (CH)

( * ) Notice: Subject to any disclaimer, the term of this patent is extended or adjusted under 35 U.S.C. 154(b) by 175 days.

(21) Appl. No.: 14/949,019

(22) Filed: Nov. 23, 2015

(65) Prior Publication Data

US 2016/0095899 A1 Apr. 7, 2016

Related U.S. Application Data

(60) Division of application No. 14/206,354, filed on Mar. 12, 2014, now Pat. No. 9,193,773, which is a division of application No. 13/284,383, filed on Oct. 28, 2011, now Pat. No. 8,703,144, which is a division of application No. 11/226,162, filed on Sep. 14, 2005, now Pat. No. 8,075,897, which is a continuation-in-part of application No. PCT/IB2004/001300, filed on Mar. 15, 2004, which is a continuation of application No. 10/799,514, filed on Mar. 12, 2004, now Pat. No. 7,923,209.

(60) Provisional application No. 60/455,004, filed on Mar. 14, 2003.

(51) Int. Cl.
| | | |
|---|---|---|
| A61K 38/16 | (2006.01) | |
| A61K 39/35 | (2006.01) | |
| C07K 14/415 | (2006.01) | |
| C07K 14/435 | (2006.01) | |

(52) U.S. Cl.
CPC ............ *A61K 38/168* (2013.01); *A61K 39/35* (2013.01); *C07K 14/415* (2013.01); *C07K 14/43531* (2013.01); *C07K 14/43563* (2013.01); *C07K 14/43572* (2013.01)

(58) Field of Classification Search
None
See application file for complete search history.

(56) References Cited

U.S. PATENT DOCUMENTS

| | | |
|---|---|---|
| 4,473,495 A | 9/1984 | Patterson |
| 5,124,249 A | 6/1992 | Khan et al. |
| 5,152,980 A | 10/1992 | Strom et al. |
| 5,723,582 A | 3/1998 | Ishizaka |
| 5,767,075 A | 6/1998 | Avruch et al. |
| 5,965,709 A | 10/1999 | Presta et al. |
| 6,042,831 A | 3/2000 | Beretta |
| 6,071,522 A | 6/2000 | Thomas et al. |
| 6,074,673 A | 6/2000 | Guillen |
| 6,395,306 B1 | 5/2002 | Cui et al. |
| 6,649,166 B1 | 11/2003 | Maillere et al. |
| 2002/0193295 A1 | 12/2002 | Calenoff et al. |
| 2003/0165514 A1 | 9/2003 | Spertini |
| 2003/0211510 A1 | 11/2003 | Henderson et al. |
| 2004/0023291 A1 | 2/2004 | Spertini |
| 2005/0249742 A1 | 11/2005 | Ruprecht et al. |

FOREIGN PATENT DOCUMENTS

| | | |
|---|---|---|
| GB | 2 341 389 A | 3/2000 |
| JP | 5390742 B2 | 1/2014 |
| WO | WO-93/19178 A2 | 9/1993 |
| WO | WO-99/18983 A1 | 4/1999 |
| WO | WO-99/34826 A1 | 7/1999 |
| WO | WO-00/15774 A1 | 3/2000 |
| WO | WO-00/44887 A1 | 8/2000 |
| WO | WO-01/88085 A2 | 11/2001 |

OTHER PUBLICATIONS

European Search Report for 10 011 428.9, dated Aug. 2, 2011.
Fasler et al., "Peptide-Induced Anergy in Allergen-Specific Human Th2 Cells Results in Lack of Cytokine Production and B Cell Help for IgE Synthesis," *Jour. of Immun.*, 155:4199-4206 (1995).
O'Brien et al., "Allergen-Specific Production of Interferon-γ by Peripheral Blood Mononuclear Cells and CD8 T Cells in Allergic Disease and Following Immunotherapy," *Clinical and Experimental Allergy*, 30:333-340 (1999).
Olaguibel et al., "Immunotherapy with Standardized Extract of Dermatophagoides Pteronyssinus in Bronchial Asthma: a Dose-Titration Study," *Allergy*, 52:168-178 (1997).
Chua et al., IgE binding studies with large peptides expressed from Derp II cDNA constucts,: *Clinical and Experimental Allergy*, 21:161-166 (1991).
Harris et al., "Prediction of murine MHC class I epitopes in a major house dust mite allergen and induction of T1-type CD8+ T cell responses," *International Immunology*, 9(2):273-280 (1997).
O'Brien et al., "An immunogenetic analysis of the T-cell recognition of the major house dust mite allergen Der p 2: identification of high- and low-responder HLA-DQ alleles and localization of T-cell epitopes," *Immunology*, 86:176-182 (1995).
Takai et al., "Non-anaphylactic combination of partially deleted fragments of the major house dust mite allergen Der f 2 for allergen-specific immunotherapy," *Molecular Immunology*, 36:1055-1065 (1999).
Thomas et al., "House-dust-mite allergens," *Allergy*, 53:821-832 (1998).
Mizumoto et al., "Analysis of T Cell Epitopes on Birch Pollen Allergy," *J. Med. Sci.*, 72(1):56-97 (1997).
O'Brien et al., "An immunogenetic analysis of T-cell reactive regions on the major allergen from the house dust mite Derp I, with recombinant truncated fragments," *J. Allergy Clin. Immunol*, 93:628-634 (1994).

(Continued)

*Primary Examiner* — Nora Rooney
(74) *Attorney, Agent, or Firm* — Marshall, Gerstein & Borun LLP

(57) ABSTRACT

The present invention relates generally to in vivo methods and compositions designed for allergen specific immunotherapy. The compositions include contiguous overlapping peptide fragments which together form an entire amino acid sequence of an allergen.

1 Claim, 8 Drawing Sheets

(56) References Cited

OTHER PUBLICATIONS

Smith, TWR, "An update on allergens: House-dust-mite allergens," *Allergy*, 53:821-832 (1998).
Spertini et al., "Allergen Peptide Immunotherapy: Results of a Safety and Immunogenicity Trial with Phospholipase A-23 Derived Long Peptides in Bee Venom Hypersensitive Patents," Abstracts: *J. Allergy Clin. Immunol*, 104(1):1106 (2000).
Akdis et al., "Epitope-Specific T Cell Toleranace to Phosholipase A(2) in Bee Venom Immunotherapy and Recovery by IL-2 and IL-15 in Vitro," *J. Clin. Invest.*, 98:1676-83, 1996.
Akdis et al., "Role of Interleukin 10 in Specific Immunotherapy," *J. Clin. Invest.*, 102:98-106, 1998.
Akdis, et al., "IL-10-Induced Anergy in Peripheral T Cell and Reactivation by Microenvironmental Cytokines: Two Key Steps in Specific Immunotherapy," *FASEB J.*, 13:603-609, 1999.
Astori, et al., "Inducing Tolerance by Intranasal Administration of Long Peptides in Naive and Primed CBA/J Mice," *J. Immunol*, 165: 3497-3505, 2000.
Attwood, T. "The Babel of Bioinformatics," *Science* 290 (5491): 471-473, 2000.
Banks, et al. in Piek T., ed. "Chemistry and Pharmacology of Honey-Bee Venom," *Venoms of the Hymenoptera*, London: Academic Press, 329-416, 1986.
Bauer et al., "Modulation of the Allergic Immune Response in BALB/c Mice by SubcutaneoInjection of High Doses of the Dominant T Cell Epitope from the Major Birch Pollen Allergen Bet v 1," *Clin. Exp. Immunol.*, 107:536-41, 1997.
Briner et al., "Peripheral T-Cell Tolerance Induced in Naive and Primed Mice by SubcutaneoInjection of Peptides from the Major Cat Allergen Fel d 1," *Proc. Natl. Acad. Sci. USA*, 90:7608-12, 1993.
Burks, et al., "Mapping and Mutational Analysis of the IgE-Binding Epitopes on Ara h 1, a Legume Vicilin Protein and a Major Allergen in Peanut Hypersensitivity," *Eur. J. Biochem*, 245: 334-339, 1997.
Casari et al., "A Method to Predict Functional Residues in Proteins," *Structural Biology*, 2(2):171-178, Feb. 1995.
Colman, "Effects of Amino Acid Sequence Changes on Antibody-Antigen Interactions," *A Structural View of Immune Recognition by Antibodies*, Biomolecular Research Institute, 33-35, 1988.
De Waal et al., "Direct Effects of IL-10 on Subsets of Human CD4+ T Cell Clones and Resting T Cells. Specific Inhibition of IL-2 Production and Proliferation," *J. Immunol.*, 150:4754-65, 1993.
Fasler et al., "Antagonistic Peptides Specifically Inhibit Proliferation, Cytokine Production, CD40L Expression, and Help for IgE Synthesis by Der P 1-Specific Human T-cell Clones," *J. Allergy Clin. Immunol.* 101: 521-530, 1998.
Fellarth, et al., "Allergen-Specific T-Cell Tolerance Induction with Allergen-Derived Long Synthetic Peptides: Results of a Phase I Trial," *J. Allergy Clin. Immunol.*, 111(4): 854-861, 2003.
Ferreira et al., "Dissection of Immunoglobulin E and T Lymphocyte Reactivity of Isoforms of the Major Birch Pollen Allergen Bet v 1: Potential Use of Hypoallergenic Isoforms for Immunotherapy," *J. Exp. Med.*, 183:559-609, Feb. 1996.
Ferreira et al., "Modulation of IgE Reactivity of Allergens by Site-Directed Mutagenesis: Potential Use of Hypoallergenic Variants for Immunotherapy," *The FASEB Journal*, 12:231-242, Feb. 1998.
Groux et al., "Interleukin-10 Induces a Long-Term Antigen-Specific Anergic State in Human CD4+ T Cells," J. Exp. Med., 184:19-29, 1996.
Hansen et al., "Allergen-Specific Th1 Cells Fail to Counterbalance Th2 Cell-Induced Airway Hyperreactivity but Cause Severe Airway Inflammation," *J. Clin. Invest.* 103:175-83, 1999.
Haselden, et al., "Immunoglobulin E-Independent Major Histocompatibility Complex-Restricted T Cell Peptide Epitope-Induced Late Asthmatic Reactions," *J. Exp. Med.*, 189:1885-94, 1999.
Hoyne et al., "Regulation of House Dust Mite Responses by Intranasally Administered Peptide: Transient Activation of CD4+ T Cells Precedes the Development of Tolerance in Vivo," *Int. Immunol.*, 8:335-42, 1996.
International Preliminary Report on Patentability from PCT/IB04/01300 dated Oct. 10, 2004.
Jilek, et al., "Antigen-Independent Suppression of the Allergic Immune Response to Bee Venom Phospholipase A2 by DNA Vaccination in CBA/J Mice," *J. Immunol.*, 166: 3612-3621, 2001.
Jutel, et al., "Selective Restimulation of Antigen or Allergen Preactivated T Cells Using OKT3 F(ab)(2) Results in the Secretion of TH-1 or TH-2-Like Cytokine Patterns," *Clin. Experiment. Allergy*, 25:1108-17, 1995.
Jutel, et al., "Bee Venom Immunotherapy Results in Decrease of IL-4 and IL-5 and Increase of IFN-γ Secretion in Specific Allergen-Stimulated T-Cell Cultures," *J. Immunol* 154: 4187-4194, 1995.
Kammerer, et al., "Modulation of T-Cell Response to Phospholipase A2 and Phospholipase A2-Derived Peptides by Conventional Bee Venom Immunotherapy," *J. Allergy Clin Immunol.*, 100(1): 96-103, 1997.
Kammerer et al., "Delineation of PLA2 Epitopes Using Short or Long Overlapping Synthetic Peptides: Interest for Specific Immunotherapy," *Clin. Exper. Allergy.*, 27: 1016-1026, 1997.
Kettner, et al., "IgE and T-Cell Responses to High-Molecular Weight Allergens from Bee Venom," *Clin. Experiment. Allergy*, 29:394-401, 1999.
Kettner, et al., Api m 6: A New Bee Venom Allergen, *J. Allergy Clin. Immunol.*, 107(5): 914-920, 2001.
King et al., "Antibody Responses to Bee Melittin (Api m 4) and Hornet Antigen 5 (Dol m 5) in Mice Treated with the Dominant T-Cell Epitope Peptides," *J. Allerg. Clin. Immunol.*, 101:397-403, 1998.
Larche, "Allergen-Derived T Cell Peptides in Immunotherapy," *Revue Francaise D'Allergologie et D'Immunologie Clinique* 2003 France, 43(1):59-63, 2003.
Larche, "Peptide-Based Therapeutic Vaccines for Allergic and Autoimmune Diseases," *Nat. Med.*, 11(4 Suppl):S69-76, 2005.
Laver et al., "Epitopes on Protein Antigens: Misconceptions and Realities," *Cell*, 61:553-556, May 1990.
Lesourd et al., "Hymenoptera Venom Immunotherapy: Relationships with Specific Antibody Responses," *J. Allergy Clin. Immunol.*, 83:563-71, 1989.
Malvey et al., "Peripheral Immune Tolerance Blocks Clonal Expansion but Fails to Prevent the Differentiation of Th1 Cells," *J. Immunol.*, 161:2168-77, 1998.
Mueller, "Diagnosis and Treatment of Insect Sensitivity," *J. Asthma Res.*, 3:331-3, 1966.
Müller et al., "Immunotherapy with Honeybee Venom and Yellow Jacket Venom is Different Regarding Efficacy and Safety," *J. Allergy Clin. Immunol.*, 89:529-35, 1992.
Müller, *Insect Sting Allergy: Clinical Picture, Diagnosis and Treatment*, Stuttgart, New York:1990.
Müller et al., "Position Paper: Immunotherapy with Hymenoptera Venoms," *Allergy*, 48(Suppl. 14):37-46, 1993.
Müller et al., "Predictive Value of Venom-Specific IgE, IgG and IgG Subclass Antibodies in Patients on Immunotherapy with Honey Bee Venom," *Allergy*, 44:412-8, 1989.
Müller et al., "Type I Skin Reactivity to Native and Recombinant Phospholipase A(2) from Honeybee Venom is Similar," *J. Allerg. Clin. Immunol.*, 96:395-402, 1995.
Muller. et al., "Successful Immunotherapy with T-Cell Epitope Peptides of Bee Venom Phospholipase A2 Induces Specific T-Cell Anergy in Patients Allergic to Bee Venom," *J. Allergy Immunol* 101: 747-754, 1998.
Ngo, et al., "Computational Complexity Protein Structure Prediction, and the Leventhal Paradox," *The Protein Folding Problem and Tertiary Structure Prediction*, Merz et al., Birkhauser, Boston, MA 433, 492-495, 1994.
Norman et al., "Treatment of Cat Allergy with T-Cell Reactive Peptides," *Am. J. Respir. Crit. Care Med.*, 154:1623-8, 1996.
Oldfield, et al., "Allergen-Derived T Cell Peptide-Induced Late Asthmatic Reactions Precede the Induction of Antigen-Specific Hyporesponsiveness in Atopic Allergic Asthmatic Subjects," *J. Immunol.*, 167:1734-9, 2001.
Ollert et al., "Prognostic Value of Immunoblotting in Patients on Immunotherapy with Hymenoptera Venom," *J. Allergy Clin. Immunol.*, 105:S59, Abstract 178, 2000.

(56) References Cited

OTHER PUBLICATIONS

Pape, et al., "Direct Evidence that Functionally Impaired CD4+ T Cells Persist in Vivo Following Induction of Peripheral Tolerance," *J. Immunol.*, 160:4719-29, 1998.

Punnonen, "Molecular Breeding of Allergy Vaccines and Antiallergic Cytokines," *International Archives of Allergy and Immunology*, 121(3):173-182, 2000.

Roggero et al., "A Simple and Rapid Procedure for the Purification of Synthetic Polypeptides by a Combination of Affinity Chromatography and Methionine Chemistry," *FEBS Letters*, 408:285-8, 1997.

Rueff et al., "Ultrarush Immunotherapy in Patents with Hymenoptera Venom Allergy," *J. Allergy Clin. Immunol.*, 107:928-9, 2001.

Schneider et al., "Human Monoclonal or Polyclonal Antibodies Recognize Predominantly DiscontinuoEpitopes on Bee Venom Phospholipase A$_2$," *J. Allergy Clin. Immunol.*, 94(1):61-70, Jul. 1994.

Secrist, et al., "Allergen Immunotherapy Decreases Interleukin 4 Production in CD4+ T-Cells From Allergic Individuals," *J. Exp Med.*, 178: 2123-2130, 1993.

Skolnick et al., "From Genes to Protein Structure and Function: Novel Applications of Computational Approaches in the Genomic Era," *Trends in Biotech*, 18(1)34-38, 2000.

Smith et al., "Recombinant Allergens for Immunotherapy: A Der p2 Variant with Reduced IgE Reactivity Retains T-Cell Epitopes," *J. Allergy Clin. Immunol.*, 101(3):423-425, 1998.

Spertini et al., "Allergen Derived Long Peptide Immunotherapy in Bee Venom Hypersensitive Patients," Abstract Presented at the Swiss Society for Immunology, Basel, Apr. 6-7, 2000 and published in *Allergologie*, p. 156, Mar. 23, 2000.

Spertini et al., "Bee Venom Desensitization: an Allergen-Derived Long Peptide Based-Immunotherapy," Abstract Berlin Presented at the EAACI (Eur. Acad. Allerg. Clin. Immunol.) Congress, Berlin, May 9-13, 2001 and published in *Allergy* 52(supp 68): 38.

Spertini et al., Allergen Derived Long Peptide Immunotherapy in Bee Venom Hypersensitive Patients, Abstract ICACI Sydney Presented at the XVII ICACI (Intl Congress Allergol. Clin. Immunol.) Sydney, Aus. Oct. 15-20, 2000, and published in *Allergy* and *Clin Immunol Int*.

Spertini et al., Allergen Peptide Immunotherapy: Results of a Safety and Immunogenicity Trial with Phospholipase A-2 Derived Long Peptides in Bee Venom Hypersensitive Patients, Abstract AAAI presented at AAAAI (American Academy Allergy Asthma and Immunol.) San Diego, Mar. 3-8, 2000 and published in *J. Allergy Clin Immuno* 105: S278.

Stanely, et al., "Identification and Mutational Analysis of the Immunodominant IgE Binding Epitopes of the Major Peanut Allergen Ara h 2," *Arch. Biochem Bipphys* 342(2): 224-253, 1997.

Swoboda et al., "Isoforms of Bet v 1, The Major Birch Pollen Allergen, Analyzed by Liquid Chromotography, Mass Spectrometry, and cDNA Cloning," *J. Biol. Chem* 270(6); 2607-2613, 1995.

Takai et al., Engineering of the Major House Dust Mite Allergen Der f 2 for Allergen-Specific Immunotherapy, *Nature Biotechnology*, 15:754-758, Aug. 1997.

Tsitoura et al., "Intranasal Exposure to Protein Antigen Induces Immunological Tolerance Mediated by Functionally Disabled CD4+ T Cells," *J. Immunol.*, 163:2592-600, 1999.

Urbanek et al., "Sub-Class of IgG Anti-Bee Venom Antibody Produced During Bee Venom Immunotherapy and Its Relationship to Long-Term Protection from Bee Stings and Following Termination of Venom Immunotherapy," *Clin. Allergy*, 16:317-22, 1986.

Van Neerven et al., "Characterization of Cat Dander-Specific T Lymphocytes from Atopic Patients," *J. Immunol.*, 152:4203-10, 1994.

Van Neerven et al., "T Cell Epitopes of House Dust Mite Major Allergen Der p II," *J. Immunol.*, 151:2326-35, 1993.

Van Regenmortel, "Structural and Functional Approaches to the Study of Protein Antigenicity," *Immunology Today*, 10(8):266-272, 1989.

Von Garnier, et al., Allergen-Derived Long Peptide Immunotherapy Down-Regulates Specific IgE Response and Protects from Anaphylaxis, *Eur. J. Immunol* 30: 1638-1645 (2000).

Written Opinion from PCT/IB04/01300 dated Oct. 4, 2004.

Zeiler et al., "Recombinant allergen fragments as candidate preparations for allergen Immunotherapy", *J. Allergy Clin. Immunol.*, vol. 100, No. 6, Part 1, pp. 721-727 (1997).

ALLERGEN PEPTIDE FRAGMENTS AND USE THEREOF FOR TREATMENT OF BIRCH POLLEN ALLERGIES

CROSS-REFERENCE TO RELATED APPLICATIONS

This is a divisional of U.S. application Ser. No. 14/206,354, filed Mar. 12, 2014, which is a divisional of U.S. application Ser. No. 13/284,383 filed Oct. 28, 2011 which is a divisional of U.S. application Ser. No. 11/226,162 filed Sep. 14, 2005, now U.S. Pat. No. 8,075,897, which is a continuation-in-part of International Application No. PCT/IB2004/01300 filed Mar. 15, 2004, which is a continuation of U.S. application Ser. No. 10/799,514 filed Mar. 12, 2004, now U.S. Pat. No. 7,923,209, which in turn claims the priority benefit under 35 U.S.C. §119(e) of U.S. provisional application Ser. No. 60/455,004 filed Mar. 14, 2003 the disclosures of which are hereby incorporated by reference. This also is a continuation-in-part of U.S. application Ser. No. 10/799,514 filed Mar. 12, 2004, now U.S. Pat. No. 7,923,209, which in turn claims the priority benefit under 35 U.S.C. §119(e) of U.S. provisional application Ser. No. 60/455,004 filed Mar. 14, 2003 the disclosures of which are hereby incorporated by reference.

INCORPORATION BY REFERENCE OF MATERIAL SUBMITTED ELECTRONICALLY

Incorporated by reference in its entirety is a computer-readable sequence listing submitted concurrently herewith and identified as follows: File Name: 41486F_SeqListing.txt; Size: 25,940 bytes; Created Nov. 23, 2015

FIELD OF THE INVENTION

The present invention relates generally to in vivo methods and compositions designed for allergen-specific immunotherapy. The compositions include contiguous overlapping peptide fragments which together comprise the entire amino acid sequence of an allergen.

BACKGROUND OF THE INVENTION

IgE-mediated allergies represent a major health problem in the industrialized world. The immediate symptoms of the disease (e.g. allergic rhinoconjunctivitis, dermatitis, bronchial asthma, anaphylactic shock) are caused by the cross-linking of effector cell-bound IgE antibodies by allergens, which leads to the release of biological mediators such as histamine or leukotrienes. In order to induce strong effector cell activation, and inflammatory responses, an allergen must be able to cross-link effector cell-bound IgE antibodies efficiently.

Allergy immunotherapy (allergy shots) is a treatment that involves injections of small amounts of the allergens to which a person is allergic. Over time, the concentration of the injections is increased, which leads to the production of blocking antibodies (called IgG antibodies, mainly IgG4 antibodies in humans) and a decrease in the level of allergic antibodies (IgE antibodies). In this way immunity is developed (e.g., a person may require allergy immunotherapy against grass, weed and tree pollens, house dust mites, cat and dog dander and insect stings).

This form of treatment varies in efficacy among different types of allergy and between individuals. Pollen, dust mite, dander and insect venom allergic reactions usually respond well. Current research involves determining exactly which mechanisms are active in a specific patient so allergen immunotherapy is better tailored to the individual. Also, work is ongoing to better define chemically the allergens used for treatment, to make allergen immunotherapy safer, and to safely increase the interval between injections.

Immunologic mechanisms of desensitization are still incompletely understood, although they appear to be associated with a Th2 to Th1 cytokine shift, with a decrease in the levels of allergen-specific IgE, and with a marked decrease in T cell response to the allergen, eventually leading to T cell tolerance (Secrist et al., J. Exp. Med. 178:2123, 1993; Jutel et al., J. Immunol. 154:4187, 1995; Kammerer et al., J. Allergy Clin. Immunol. 100:96, 1997; Akdis et al., FASEB J. 13:603, 1999; and Muller et al., J. Allergy Clin. Immunol 101:747, 1998). This may, directly or indirectly, contribute to decreased mast cell or eosinophil activation and may also improve patient protection upon reexposure to the allergen (Jutel et al., Clin. Exp. Allergy 26:1112 1996).

Safer methods of immunotherapy with reduced risk of anaphylaxis need to be developed.

SUMMARY OF THE INVENTION

In one aspect, the invention provides a composition containing a plurality of contiguous overlapping peptide fragments (SEQ ID NOs: 1, 2 and 3) which together comprise the entire amino acid sequence of a bee venom allergen (SEQ ID NO: 4), wherein the fragments are capable of inducing a T cell response in patients who are hypersensitive to the allergen.

In another aspect, the invention provides a composition containing a plurality of contiguous overlapping peptide fragments (SEQ ID NOs: 5 and 6) which together comprise the entire amino acid sequence of a birch pollen allergen (SEQ ID NO: 7), wherein the fragments are capable of inducing a T cell response in patients who are hypersensitive to the allergen.

In yet another aspect, the invention provides a composition containing a plurality of contiguous overlapping peptide fragments (SEQ ID NOs: 8 and 9) which together comprise the entire amino acid sequence of a birch pollen profilin allergen (SEQ ID NO: 10), wherein the fragments are capable of inducing a T cell response in patients who are hypersensitive to the allergen.

In a further aspect, the invention provides a composition containing a plurality of contiguous overlapping peptide fragments (SEQ ID NOs: 11, 12 and 13) which together comprise the entire amino acid sequence of a dust mite allergen (SEQ ID NO: 14), wherein the fragments are capable of inducing a T cell response in patients who are hypersensitive to the allergen.

In yet another aspect, the invention provides a composition containing a plurality of contiguous overlapping peptide fragments (SEQ ID NOs: 15 and 16) which together comprise the entire amino acid sequence of a dust mite allergen (SEQ ID NO: 17), wherein the fragments are capable of inducing a T cell response in patients who are hypersensitive to the allergen.

In yet another aspect, the invention provides a composition containing a plurality of contiguous overlapping peptide fragments (SEQ ID NOs: 5 and 8) which together comprise the entire amino acid sequence of a chimeric birch pollen allergen (SEQ ID NO: 18), wherein the fragments are capable of inducing a T cell response in patients who are hypersensitive to the allergen.

In yet another aspect, the invention provides a composition containing a plurality of contiguous overlapping peptide fragments (SEQ ID NOs: 9 and 6) which together comprise the entire amino acid sequence of a chimeric birch pollen allergen (SEQ ID NO: 19), wherein the fragments are capable of inducing a T cell response in patients who are hypersensitive to the allergen.

In yet another aspect, the invention provides a composition containing a plurality of contiguous overlapping peptide fragments (SEQ ID NOs: 8 and 5) which together comprise the entire amino acid sequence of a chimeric birch pollen allergen (SEQ ID NO: 20), wherein the fragments are capable of inducing a T cell response in patients who are hypersensitive to the allergen.

In yet another aspect, the invention provides a composition containing a plurality of contiguous overlapping peptide fragments (SEQ ID NOs: 6 and 9) which together comprise the entire amino acid sequence of a chimeric birch pollen allergen (SEQ ID NO: 21), wherein the fragments are capable of inducing a T cell response in patients who are hypersensitive to the allergen.

In yet another aspect, the invention provides a composition containing a plurality of contiguous overlapping peptide fragments (SEQ ID NOs: 15 and 11) which together comprise the entire amino acid sequence of a chimeric dust mite allergen (SEQ ID NO: 22), wherein the fragments are capable of inducing a T cell response in patients who are hypersensitive to the allergen.

In yet another aspect, the invention provides a composition containing a plurality of contiguous overlapping peptide fragments (SEQ ID NOs: 13 and 16) which together comprise the entire amino acid sequence of a chimeric dust mite allergen (SEQ ID NO: 23), wherein the fragments are capable of inducing a T cell response in patients who are hypersensitive to the allergen.

Preferably, administration of the compositions of the invention results in lower levels of IgE stimulation activity. More preferably, administration results in weak or zero IgE stimulation activity (e.g. weak IgE binding or no IgE binding). As used herein, weak IgE binding refers to IgE production and/or cross-linking that is less than the amount of IgE production and/or IL-4 production stimulated by the whole protein allergen. Preferably, the compositions of the invention do not induce immediate skin reactivity (wheal <5 mm with no flare) when injected intradermally at a concentration ≤1 µg/ml. Most preferably, administration of the compositions of the invention results in a decrease in T cell response upon subsequent exposure to the protein allergen, thereby modulating an immune response of a patient against the protein allergen.

In another aspect, the invention provides in vivo methods of determining the dose of composition needed to desensitize a patient to a specific allergen by introducing a series of compositions containing varying concentrations of a plurality of contiguous overlapping peptide fragments, which together comprise the entire amino acid sequence of the allergen, into the skin of the patient, wherein the fragments are capable of inducing a T cell response in patients who are hypersensitive to the allergen, further wherein said overlapping peptide fragments do not bind or weakly bind IgE; introducing a positive-control and a negative-control into the skin of the patient; checking for development of a wheal or flare at the introduction site; and comparing the size of the papule (<5 mm) and flare produced by the varying concentrations of a plurality of contiguous overlapping peptide fragments to the positive-control and negative-control, thereby determining the dose of composition needed to desensitize the patient to the specific allergen. For example, the patient is selected from the group consisting of humans, dogs, cats, pigs, horses, rats and mice. In one preferred embodiment, the patient is a human. In some embodiments, each peptide of the plurality of contiguous overlapping peptide fragments can be 30-90 amino acids in length, e.g., 30, 35, 40, 45, 50, 55, 60, 65, 70, 73, 75, 80, 81, 85, 86 and 90 amino acids in length. In various embodiments, the amino acid sequences of contiguous overlapping peptide fragments in the plurality overlap by from 5 to 25 amino acids with overlaps of 9 to 22 amino acids being preferred with overlaps of from about 10 to about 15 amino acids, e.g., 10, 11, 12, 13, 14 and 15 amino acids being particularly preferred.

The methods of the invention are useful in treating a number of different allergies to various allergens. For example, the allergens include, but are not limited to, plant pollens, grass pollens, tree pollens, weed pollens, insect venom, dust mite proteins, animal dander, saliva, fungal spores and food allergens (i.e., peanut, milk, gluten and egg). In one embodiment, the allergen is insect venom. In one preferred embodiment, the insect venom is bee venom. The plurality of contiguous overlapping peptide fragments may include SEQ ID NOs: 1, 2, and 3, which comprise the entire amino acid sequence of the major bee venom allergen (SEQ ID NO: 4). In another embodiment, the allergen is tree pollen. In one preferred embodiment, the tree pollen is birch pollen. The plurality of contiguous overlapping peptide fragments may include SEQ ID NOs: 5 and 6, which comprise the entire amino acid sequence of the major birch pollen allergen (SEQ ID NO: 7). The plurality of contiguous overlapping peptide fragments may include SEQ ID NOs: 8 and 9, which comprise the entire amino acid sequence of birch pollen profilin allergen (SEQ ID NO: 10). In another embodiment, the allergen is dust mite proteins. The plurality of contiguous overlapping peptide fragments may include SEQ ID NOs: 11, 12, and 13, which comprise the entire amino acid sequence of the dust mite allergen *D. pteronyssinus* 1 (SEQ ID NO:14). The plurality of contiguous overlapping peptide fragments may include SEQ ID NOs: 15 and 16, which comprise the entire amino acid sequence of the dust mite allergen *D. pteronyssinus* 2 (SEQ ID NO:17). The plurality of contiguous overlapping peptide fragments may include at least two contiguous overlapping peptide fragments selected from the group consisting of SEQ ID NOs: 1, 2, 3, 5, 6, 8, 9, 11, 12, 13, 15 and 16.

In various embodiments, the introducing is done by skin prick, intradermal or subcutaneous injection. Those skilled in the art will recognize that any means of introducing can be employed. In some embodiments, the varying concentrations of contiguous overlapping peptide fragments is from a concentration of about 0.001 µg/ml to about 100 µg/ml. In preferred embodiments, the concentration of contiguous overlapping peptide fragments are between 0.001-10.0, 0.01-10.0, or 0.1-1.0 µg/ml.

In yet another aspect, the invention provides in vivo methods of inducing tolerance in a patient allergic to a specific allergen by introducing a plurality of contiguous overlapping peptide fragments which together form an entire amino acid sequence of the allergen into the skin of the patient, wherein the fragments are capable of inducing a T cell response in patients who are hypersensitive to the allergen, further wherein said overlapping peptide fragments do not bind or weakly bind IgE; and creating antibodies to the allergen, thereby building immunity to the allergen, wherein the immunity leads to tolerance of the allergen in the patient. For example, the patient is selected from the group consisting of humans, dogs, cats, pigs, horses, rats and mice. In one preferred embodiment, the patient is a human. In another embodiment, the antibodies created to the allergen are IgG antibodies. More preferably, the IgG antibodies are IgG4 antibodies. In some embodiments, each peptide of the plurality of contiguous overlapping peptide fragments can be 30-90 amino acids in length, e.g., 30, 35, 40, 45, 50, 55, 60, 65, 70, 73, 75, 80, 81, 85, 86 and 90 amino acids in length. In various embodiments, the amino acid sequences of contiguous overlapping peptide fragments in the plurality overlap by about 10 to about 15 amino acids, e.g., 10, 11, 12, 13, 14 and 15 amino acids. In some embodiments, the varying concentrations of contiguous overlapping peptide fragments is from a concentration of about 0.001 µg/ml to about 1000 µg/ml. In preferred embodiments, the concentration of contiguous overlapping peptide fragments are between 0.001-100.0, 0.01-10.0, or 0.1-1.0 µg/ml.

The methods of the invention are useful in treating a number of different allergies to various allergens. For example, the allergens include, but are not limited to, plant pollens, grass pollens, tree pollens, weed pollens, insect venom, dust mite proteins, animal dander, saliva, fungal spores and food allergens (i.e., peanut, milk, gluten and egg). In one embodiment, the allergen is insect venom. In one preferred embodiment, the insect venom is bee venom. The plurality of contiguous overlapping peptide fragments may include SEQ ID NOs: 1, 2, and 3, which comprise the entire amino acid sequence of the major bee venom allergen (SEQ ID NO: 4). In another embodiment, the allergen is tree pollen. In one preferred embodiment, the tree pollen is birch pollen. The plurality of contiguous overlapping peptide fragments may include SEQ ID NOs: 5 and 6, which comprise the entire amino acid sequence of the major birch pollen allergen (SEQ ID NO: 7). In another preferred embodiment, the plurality of contiguous overlapping peptide fragments may include SEQ ID NOs: 8 and 9, which comprise the entire amino acid sequence of birch pollen profilin allergen (SEQ ID NO: 10). In one embodiment, the allergen is dust mite proteins. The plurality of contiguous overlapping peptide fragments may include SEQ ID NOs: 11, 12, and 13, which comprise the entire amino acid sequence of the dust mite allergen *D. pteronyssinus* 1 (SEQ ID NO:14). The plurality of contiguous overlapping peptide fragments may include SEQ ID NOs: 15 and 16, which comprise the entire amino acid sequence of the dust mite allergen *D. pteronyssinus* 2 (SEQ ID NO:17). The plurality of contiguous overlapping peptide fragments may include at least two contiguous overlapping peptide fragments selected from the group consisting of SEQ ID NOs: 1, 2, 3, 5, 6, 8, 9, 11, 12, 13, 15 and 16.

Preferably, the methods of the invention do not induce immediate skin reactivity (wheal <5 mm with no flare) when injected intradermally at a concentration 1 µg/ml.

In various embodiments, the introducing is done by parenteral, e.g., skin prick, intravenous, intradermal, subcutaneous, oral, nasal, mucosal (e.g., inhalation), transdermal (topical), transmucosal, lymph node and rectal administration. Those skilled in the art will recognize that any means of introducing can be employed.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 2B: IFN-γ; FIG. 2C: IL-10) from supernatants of short term T cell lines were measured by ELISA in cell supernatant. Results are presented as plot-boxes and whiskers with successive percentiles 5, 25, 50, 75, 95. Medians are indicated by thick bars.

DETAILED DESCRIPTION OF THE INVENTION

Figure 1:
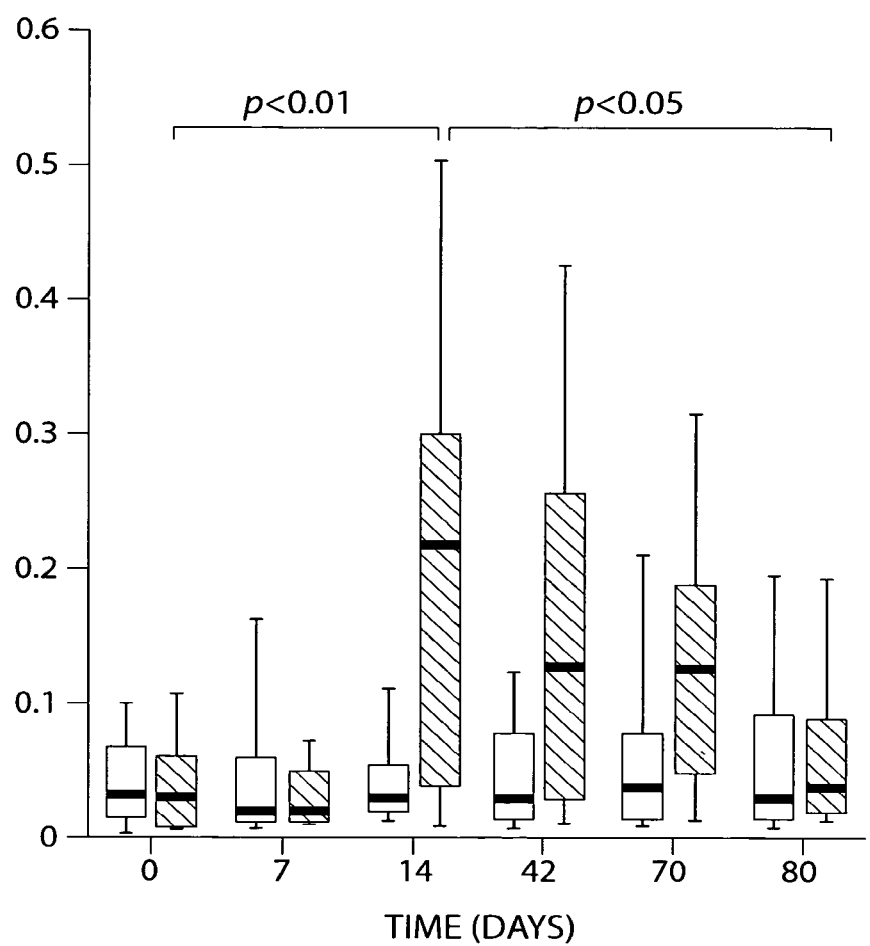
FIG. 1 is a graph showing $PLA_2$ derived overlapping peptide therapy induces specific T cell anergy in bee venom hypersensitive patients. Hatched columns: peptide-treated group, open columns: control group (treated with albumin). Results are presented as plot-boxes and whiskers with successive percentiles 5, 25, 50, 75, 95. Medians are indicated by thick bars.

The invention is based, in part, on the discovery that a plurality of contiguous overlapping peptide fragments can be used for allergen specific immunotherapy. The use of a plurality of contiguous overlapping peptide fragments for allergen immunotherapy induces both humoral and cellular responses comparable to native allergen rush immunotherapy.

Advantages of using the plurality of contiguous overlapping peptide fragments of the invention include, but are not limited to, their ability to induce a T helper cell response in hypersensitive patients due to the fact that they contain all possible T cell epitopes; their ability to efficiently recruit specific T cells, leading to a modulation of the immune response to allergens; and their ability to display low IgE binding activity (they are hypoallergenic). Thus, the plurality of contiguous overlapping peptide fragments of the invention display significantly reduced IgE binding activity, but conserved T cell activating capacity, therefore making them ideal candidates for a novel and safe approach of specific immunotherapy.

Without being limited to any particular mechanism, the ability of a plurality of contiguous overlapping peptide fragments to induce a T helper cell response in hypersensitive patients may be due to the fact that the amino acid sequence of contiguous overlapping peptide fragments in the plurality overlap by from about 5 to 25 amino acids and in particular from 9 to 22 amino acids and from about 10 to about 15 amino acids, e.g., 10, 11, 12, 13, 14 and 15 amino acids and cover multiple T cell epitopes. Therefore these combinations of peptides do not require T cell epitope customization to fit with each patient's major histocompatibility complex (MHC) molecules (HLA restriction). The ability of contiguous overlapping peptide fragments to display low IgE binding activity may be due to the fact that the contiguous overlapping peptide fragments are linear and are unable to cross-link with IgE antibodies.

One important application of the invention is to the problem of allergies to foods or materials in the surroundings. Millions of individuals are subjected to severe symptomatology in response to otherwise harmless components of the environment, for example, ragweed or other pollens. The method of the invention can prevent or diminish this immune response which results in widespread discomfort.

It is to be understood that the terminology used herein is for the purpose of describing particular embodiments only and is not intended to limit the scope of the present invention. As used herein and in the claims, the singular forms "a", "and" and "the" include plural referents unless the context clearly dictates otherwise.

The terms "human leukocyte antigen" and HLA" is here defined as a genetic fingerprint on white blood cells and platelets, composed of proteins that play a critical role in activating the body's immune system to respond to foreign organisms.

The term "plurality of contiguous overlapping peptide fragments (OPF)" is here defined as at least one, but most likely two, three, four, or five, contiguous overlapping peptide fragments. For example, the schematic below shows an example of a plurality of contiguous overlapping peptide fragments, if the alphabet was a 26 residue peptide, and the plurality contained four overlapping peptides: $OPF_{1-6}$, $OPF_{4-15}$, $OPF_{13-22}$ and $OPF_{20-26}$:

ABCDEF=$OPF_{1-6}$
DEFGHIJKLMNO=$OPF_{4-15}$
MNOPQRSTUV=$OPF_{13-22}$
TUVWXYZ=$OPF_{20-26}$

The term "hypersensitive" is here defined as abnormally susceptible physiologically to a specific agent via IgE-mediated mechanisms (as an antigen or drug). Such antigen is in the present specification and claims called an allergen.

The term "hyposensitive" is here defined as not being sensitive to a specific agent (as an antigen or drug). Such antigen is in the present specification and claims called an allergen.

The terms "desensitize", "immunological tolerance" or "tolerance" are here defined as to make (a sensitized or hypersensitive individual) insensitive or nonreactive to a sensitizing agent (as an antigen or drug) by a reduction in immunological reactivity of a host towards specific tolerated antigen(s). Such antigen is in the present specification and claims called an allergen.

The term "positive-control" is here defined as a native allergen that when applied to the skin will produce a positive reaction i.e. a red area, the flare and a raised spot, the wheal, at the test site if IgE antibody is present. Apart native allergens, examples of positive-controls include pharmacological agents such as, but not limited to, histamine. The optimal positive-control is the allergen itself in its native confirmation.

The term "negative-control" is here defined as a composition that when applied to the skin, should not produce, at 15 minutes, a response with a flare >5 mm when the injected volume of solution (50 μl) produces spontaneously a papule of 5 mm. Negative-controls include OPF diluent, albumin solution or saline (salt-water) solution.

The term "papule" is here defined as a small circumscribed, superficial, solid elevation of the skin. When related to allergens, it is usually measured by a wheal and flare reaction which is an outward spreading zone of reddening flare followed rapidly by a wheal (swelling) at the site of introduction of the allergen.

The term "erythema" is here defined as redness of the skin produced by congestion of the capillaries, which may result from a variety of causes.

The term "isolated" or "purified" peptide fragments or biologically active portion thereof is substantially free of material (e.g., other, contaminating proteins) from the cell suspension, tissue source, or serum preparation from which the allergen peptide fragments are derived, or substantially free from chemical precursors or other chemicals when chemically synthesized. The language "substantially free of other material" includes preparations of the allergen-derived peptide fragments in which the peptide fragments are separated from cellular components of the cells from which it is isolated or recombinantly produced. In one embodiment, the peptide fragments having less than about 30% (by dry weight) of non-allergen protein (also referred to herein as a "contaminating protein"), more preferably less than about 20% of non-allergen protein, still more preferably less than about 10% of non-allergen protein, and most preferably less than about 5% non-allergen protein. When the allergen-derived peptide fragments are recombinantly produced, it is also preferably substantially free of culture medium, i.e., culture medium represents less than about 20%, more preferably less than about 10%, and most preferably less than about 5% of the volume of the overlapping peptides preparation.

The language "substantially free of chemical precursors or other chemicals" includes preparations of the allergen-derived peptide fragments in which the peptide fragments are separated from chemical precursors or other chemicals which are involved in the synthesis of the protein. In one embodiment, the language "substantially free of chemical precursors or other chemicals" includes preparations of the allergen-derived peptide fragments having less than about 30% (by dry weight) of chemical precursors or non-allergen chemicals, more preferably less than about 20% chemical precursors or non-allergen chemicals, still more preferably less than about 10% chemical precursors or non-allergen chemicals, and most preferably less than about 5% chemical precursors or non-allergen chemicals.

Manipulations of the sequences included within the scope of the invention may be made at the peptide level. Included within the scope of the present invention are peptide fragments (derivative or analog thereof) that are modified during or after translation or synthesis (e.g., by glycosylation, acetylation, phosphorylation, amidation, derivatization by known protecting/blocking groups, proteolytic cleavage, linkage to an antibody molecule or other cellular ligand, and the like). Any of the numerous chemical modification methods known within the art may be utilized including, but not limited to, specific chemical cleavage by cyanogen bromide, trypsin, chymotrypsin, papain, V8 protease, NaBH.sub.4, acetylation, formylation, oxidation, reduction, metabolic synthesis in the presence of tunicamycin, etc. In a specific embodiment, sequences of a peptide are modified to include a fluorescent label Allergen-derived peptide fragments, analogs, derivatives, and variants thereof can be chemically synthesized. For example, a peptide fragment corresponding to a portion of an allergen protein that includes a desired domain or that mediates a desired activity in vitro, may be synthesized by use of a peptide synthesizer. The amino acid sequence of a protein isolated from the natural source, may be determined, e.g., by direct sequencing of the isolated protein. The protein may also be analyzed by hydrophilicity analysis (see, Hopp and Woods, PNAS USA 78:3824, 1981) which can be used to identify the hydrophobic and hydrophilic regions of the protein, thus aiding in the design of peptides for experimental manipulation, such as in binding experiments, antibody synthesis, etc. Secondary structural analysis may also be performed to identify regions of a peptide that adopt specific structural motifs. (See, Chou and Fasman, Biochem, 13:222, 1974). Manipulation, translation, secondary structure prediction, hydrophilicity and hydrophobicity profiles, open reading frame prediction and plotting, and determination of sequence homologies, can be accomplished using computer software programs available in the art. Other methods of structural analysis including, but not limited to, X-ray crystallography (see, Engstrom Biochem Exp Biol 11:7, 1974); mass spectroscopy and gas chromatography (see, Methods in Protein Science J. Wiley and Sons, New York, N.Y. 1997); computer modeling (see, Fletterick and Zoller, eds., 1986, Computer Graphics and Molecular Modeling, In: Current Communications in Molecular Biology, Cold Spring Harbor Laboratory Press, Cold Spring Harbor, N.Y.); optical rotary dispersion (ORD) and circular dichroism (CD) may also be used. For example, measurement of circular dichroism may be used to determine the linearity of candidate peptides for use as COPs.

The peptide fragments, derivatives and other variants described herein, can be modified. Thus, the invention includes, e.g., myristylated, glycosylated, palmitoylated and phosphorylated peptides and their derivatives.

Conservative amino acid substitutions can be made in the peptide fragments at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, in a peptide fragment with a conservative amino acid substitution a predicted non-essential amino acid residue in the allergen-derived fragment is preferably replaced with another amino acid residue from the same side chain family. Alternatively, in another embodiment, mutations can be introduced randomly along all or part of the allergen coding sequence, to identify mutants that retain T cell stimulating activity but have lower or reduced/weak levels of IgE stimulating activity.

In some embodiments, a mutant allergen peptide fragment can be assayed for (1) the ability to stimulate or induce T cell proliferation or (2) the ability, or lack of, to bind IgE antibodies from, e.g., the sera of an individual hypersensitive to the allergen. The terms "stimulate" or "induce" are used interchangeably herein.

A peptide fragment or combination of overlapping peptide fragments derived from a protein allergen, can be tested to determine whether the peptide will produce local or systemic symptoms that are related to a Type I reaction. This reaction involves the interaction of antigen with antibody of the immunoglobulin class IgE, which attaches to the host cells in the skin and other tissues (mast cells, basophils, platelets, and eosinophils). An antigen encounter results in release of the cell contents, including active molecules such as histamine, heparin, serotonin, and other vasoactive substances, producing local or systemic symptoms that are manifest within minutes to a few hours following antigen-IgE interaction. IgE binding activity of candidate COPs can also be measured by means of ELISA assays using IgEs specific for selected polypeptide allergens having less than a selected maximum binding affinity. According to one aspect of the invention, ELISA assays may be conducted on candidate COPS wherein COPs are selected which have a binding activity for IgE's reactive with the selected polypeptide allergen which is less than three times the standard deviation of a negative control in a conventional ELISA assay.

T cell stimulating activity can be tested by culturing T cells obtained from an individual sensitive to the allergen proteins and variants described herein (i.e., an individual who has an immune response to the protein allergen or protein antigen) with an allergen protein or variant and determining the presence or absence of proliferation by the T cells in response to the peptide as measured by, for example, incorporation of tritiated thymidine. Stimulation indices for responses by T cells to peptides useful in methods of the invention can be calculated as the maximum counts per minute (cpm) incorporated in response to the peptide divided by the cpm of the control medium. For example, a peptide derived from a protein allergen may have a stimulation index of about 2.0. A stimulation index of at least 2.0 is generally considered positive for purposes of defining peptides useful as immunotherapeutic agents. Preferred peptides or fragments or combinations of overlapping fragments have a stimulation index of at least 2.5, more preferably at least 3.5 and most preferably at least 5.0.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., percent homology equals the number of identical positions divided by the total number of positions times 100).

The invention also provides specific allergen chimeric or fusion proteins. As used herein, a specific allergen "chimeric protein" or "fusion protein" comprises, an allergen polypeptide operatively linked to a non-allergen polypeptide. An "allergen polypeptide" refers to a polypeptide having an amino acid sequence corresponding to a specific allergen, whereas a "non-allergen polypeptide" refers to a polypeptide having an amino acid sequence corresponding to a protein which is not substantially homologous to the specific allergen, e.g., a protein which is different from the allergen and which is derived from the same or a different organism. Within a specific allergen fusion protein the allergen polypeptide can correspond to all or a portion of a specific allergen protein. In a preferred embodiment, a specific allergen fusion protein comprises at least one biologically active portion of the specific allergen. The non-allergen polypeptide can be fused to the N-terminus or C-terminus of the allergen polypeptide.

Allergen Based Compositions

The contiguous overlapping allergen peptide fragments (also referred to herein as "active compounds") of the invention can be incorporated into compositions suitable for administration. Such compositions typically include the contiguous overlapping peptide fragments and a pharmaceutically acceptable carrier. The term "pharmaceutically acceptable carrier" refers to a carrier that does not cause an allergic reaction or other untoward effect in subjects to whom it is administered. Suitable pharmaceutically acceptable carriers include, for example, water, saline, phosphate buffered saline, dextrose, glycerol, ethanol, or the like, and combinations thereof. In addition, if desired, the composition can contain minor amounts of auxiliary substances such as wetting or emulsifying agents, and/or pH buffering agents which enhance the effectiveness of the vaccine. Attention is directed to Remington's Pharmaceutical Science by E. W. Martin. Immunostimulatory adjuvants are predominantly derived from pathogens, e.g., lipopolysaccharide (LPS) and monophosphoryl lipid A (MPL), which activate cells of the immune system. Bacterial CpG motifs in DNA have direct immunostimulatory effects on immune cells in vitro, the immunostimulatory effect is due to the presence of unmethylated CpG dinucleotides, which are under-represented and are methylated in vertebrate DNA. Unmethylated CpGs in the context of selective flanking sequences are thought to be recognized by cells of the immune system to allow discrimination of pathogen-derived DNA from self DNA. CpG motifs are most potent for the induction of Th1 responses, mainly through stimulating TNFβ, IL-1, IL-6 and IL-12, and through the expression of co-stimulatory molecules. CpGs also appear to have significant potential as mucosally administered adjuvants. Importantly, CpGs also appear to have significant potential for the modulation of existing immune responses, which may be useful in various clinical settings, including allergies. (See for example, O'Hagan et al., Biomolecular Engineering, 18:69-85, 2001; Singh and O'Hagan, Nature Biotechnology, 17:1075-1081, 1999).

The use of such media and agents for pharmaceutically active substances is well known in the art. Except insofar as any conventional media or agent is incompatible with the active compound, use thereof in the compositions is contemplated. Supplementary active compounds can also be incorporated into the compositions. As used herein, the phrases 'composition' and 'therapeutic composition' are interchangeable.

Compositions containing the contiguous overlapping allergen peptide fragments, or variants thereof can be administered to a patient (such as a human) sensitive to the specific allergen in a form which results in a decrease in the T cell response of the mammal upon subsequent exposure to the protein allergen. As used herein, a decrease or modification of the T cell response of a mammal sensitive to a protein allergen is defined as non-responsiveness or diminution in symptoms to the protein allergen in the patient, as determined by standard clinical procedures (see, Varney et al., British Medical Journal, 302: 265, 1990), including diminution in allergen induced asthmatic conditions. As referred to herein, a diminution in symptoms to an allergen includes any reduction in the allergic response of a patient, such as a human, to the allergen following a treatment regimen with a composition as described herein. This diminution in symptoms may be determined subjectively in a human (e.g., the patient feels more comfortable upon exposure to the allergen), or clinically, such as with a standard skin test or provocation assay.

In addition, administration of the above-described contiguous overlapping allergen peptide fragments or their variants may result in lower levels of IgE stimulation activity. Preferably, administration results in weak IgE stimulating activity. More preferably, administration results in zero IgE stimulating activity. As used herein, weak IgE stimulating activity refers to IgE production and/or cross-linking that is less than the amount of IgE production and/or IL-4 production stimulated by the whole protein allergen.

Administration of the compositions of the present invention to desensitize or tolerize an individual to a protein allergen or other protein antigen can be carried out using procedures, at dosages and for periods of time effective to reduce sensitivity (i.e., to reduce the allergic response) of the individual to a protein allergen or other protein antigen. Effective amounts of the compositions will vary according to factors such as the degree of sensitivity of the individual to the protein allergen, the age, sex, and weight of the individual, and the ability of the peptide(s) to elicit a tollerogenic response in the individual. Dosage regimens may be adjusted to provide the optimum therapeutic response. For example, several divided doses may be administered daily or the dose may be proportionally reduced as indicated by the exigencies of the therapeutic situation.

A composition of the invention is formulated to be compatible with its intended route of administration. Examples of routes of administration include parenteral, e.g., skin prick, intravenous, intradermal, subcutaneous, oral, nasal, mucosal (e.g., inhalation), transdermal (topical), transmucosal, lymph node and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of toxicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Administration, e.g., subcutaneous administration, of an allergen-derived overlapping peptide or variant peptides as described herein to a patient, such as a human, can tolerize or anergize appropriate T cell subpopulations such that they become unresponsive to the protein allergen and do not participate in stimulating an immune response upon subsequent exposure. In addition, administration of such a peptide may modify the lymphokine secretion profile as compared with exposure to the naturally-occurring protein allergen or portion thereof (e.g., result in a decrease of IL-4 and/or an increase in IL-10, TGFβ, and IFN-γ). Furthermore, exposure to the peptide may influence T cell subpopulations which normally participate in the response to the allergen such that these T cells, when re-exposed to the native allergen, are secreting high levels of IL-10, TGFβ, or IFN-γ, instead of high levels of IL-4 or IL-5. This immune deviation of T cell subpopulations may ameliorate or reduce the ability of an individual's immune system to stimulate the usual immune response at the site of normal exposure to the allergen, resulting in a diminution in allergic symptoms.

Compositions suitable for injectable use include sterile aqueous solutions (where the peptides or protein are water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., overlapping peptide fragments) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The compositions can be included in a container, pack, or dispenser together with instructions for administration.

It is also possible to modify the structure of peptides useful in methods of the invention for such purposes as increasing solubility, enhancing therapeutic or preventive efficacy, or stability (e.g., shelf life ex vivo, and resistance to proteolytic degradation in vivo). A modified peptide can be produced in which the amino acid sequence has been altered, such as by amino acid substitution, deletion, or addition, to modify immunogenicity and/or reduce allergenicity, or to which a component has been added for the same purpose. For example, the amino acid residues essential to T cell epitope function can be determined using known techniques (e.g., substitution of each residue and determination of presence or absence of T cell reactivity). Those residues shown to be essential can be modified (e.g., replaced by another amino acid whose presence is shown to enhance T cell reactivity), as can those which are not required for T cell reactivity (e.g., by being replaced by another amino acid whose incorporation enhances T cell reactivity but does not diminish binding to relevant MHC molecules). Another example of a modification of peptides is substitution of cysteine residues preferably with alanine, or alternatively with serine or threonine to minimize dimerization via disulfide linkages.

In order to enhance stability and/or reactivity, peptides can also be modified to incorporate one or more polymorphisms in the amino acid sequence of a protein allergen resulting from natural allelic variation. Additionally, D-amino acids, non-natural amino acids or non-amino acid analogues can be substituted or added to produce a modified synthetic peptide within the scope of this invention.

In some embodiments, the peptides can be synthesized as retro-inverso peptides. (See Sela and Zisman, FASEB J. 11:449, 1997). Evolution has ensured the almost exclusive occurrence of L-amino acids in naturally occurring proteins. Virtually all proteases therefore cleave peptide bonds between adjacent L-amino acids; thus, artificial proteins or peptides composed of D-amino acids are largely resistant to proteolytic breakdown. This resistance has been attractive to drug designers, but the exclusivity of biological systems for proteins made of L-amino acids means that such proteins cannot interact with the mirror image surface formed by enantiomeric proteins. Thus, an all D-amino acid protein usually has no biological effect or activity.

Linear modified retro-peptide structures have been studied for a long time (See Goodman et al., Accounts of Chemical Research, 12:1-7, 1979) and the term "retro-isomer" was designated to include an isomer in which the direction of the sequence is reversed compared with the parent peptide. By "retro-inverso isomer" is meant an isomer of a linear peptide in which the direction of the sequence is reversed and the chirality of each amino acid residue is inverted; thus, there can be no end-group complementarity.

More recently, Jameson et al. engineered an analogue of the hairpin loop of the CD4 receptor by combining these two properties: reverse synthesis and a change in chirality. See Jameson et al., Nature 368:744-746, 1994 and Brady et al., Nature, 368:692-693, 1994. The net result of combining D-enantiomers and reverse synthesis is that the positions of carbonyl and amino groups in each amide bond are exchanged, while the position of the side-chain groups at each alpha carbon is preserved. Jameson et al. demonstrated an increase in biological activity for their reverse D peptide, which contrasts to the limited activity in vivo of its conventional all-L enantiomer (due to its susceptibility to proteolysis).

A partially modified retro-inverso pseudopeptide has been reported for use as a non-natural ligand for the human class I histocompatibility molecule, HLA-A2. (See Guichard et al., Med. Chem. 39:2030-2039, 1996). Such non-natural ligands had increased stability and high MHC-binding capacity.

Retro-inverso peptides are prepared for peptides of known sequence in the following manner. A peptide having a known sequence (e.g., a tumor antigen peptide) is selected as a model peptide for designing and synthesizing a retro-inverso peptide analog. The analog is synthesized using D-amino acids by attaching the amino acids in a peptide chain such that the sequence of amino acids in the retro-inverso peptide analog is exactly opposite of that in the selected peptide which serves as the model. To illustrate, if the peptide model is a peptide formed of L-amino acids having the sequence ABC, the retro-inverso peptide analog formed of D-amino acids would have the sequence CBA. The procedures for synthesizing a chain of D-amino acids to form the retro-inverso peptides are known in the art and are illustrated in the above-noted references.

Since an inherent problem with native peptides is degradation by natural proteases, the peptides of the invention may be prepared to include the "retro-inverso isomer" of the desired peptide. Protecting the peptide from natural proteolysis should therefore increase the effectiveness of the specific heterobivalent or heteromultivalent compound.

A higher biological activity is predicted for the retro-inverso containing peptide when compared to the non-retro-inverso containing analog owing to protection from degradation by native proteinases.

Furthermore, peptides can be modified to produce a peptide-PEG conjugate.

Modifications of peptides can also include reduction/alkylation (Tarr in: Methods of Protein Microcharacterization, J. E. Silver, ed. Humana Press, Clifton, N.J., pp 155-194, 1986); acylation (Tan, supra); esterification (Tan, supra); chemical coupling to an appropriate carrier (Mishell and Shiigi, eds., Selected Methods in Cellular_Immunology, WH Freeman, San Francisco, Calif.; U.S. Pat. No. 4,939, 239, 1980); or mild formalin treatment (Marsh International Archives of Allergy and Applied Immunology, 41:199, 1971).

To facilitate purification and potentially increase solubility of peptides, it is possible to add reporter group(s) to the peptide backbone. For example, poly-histidine can be added to a peptide to purify the peptide on immobilized metal ion affinity chromatography. (See Hochuli et al., Bio/Technology, 6:1321, 1988). In addition, specific endoprotease cleavage sites can be introduced, if desired, between a reporter group and amino acid sequences of a peptide to facilitate isolation of peptides free of irrelevant sequences. In order to successfully desensitize an individual to a protein antigen, it may be necessary to increase the solubility of a peptide by adding functional groups to the peptide or by not including hydrophobic T cell epitopes or regions containing hydrophobic epitopes in the peptide.

To aid proper antigen processing of T cell epitopes within a peptide, canonical protease sensitive sites can be recombinantly or synthetically engineered between regions, each comprising at least one T cell epitope. For example, charged amino acid pairs, such as KK or RR, can be introduced between regions within a peptide during synthesis.

The invention further encompasses at least one therapeutic composition useful in treating a condition which involves an immune response to a protein antigen (e.g., an allergen, an autoantigen, etc.) comprising at least one peptide having a sufficient percentage of the T cell epitopes of the protein antigen such that in a substantial percentage of a population of individuals sensitive to the protein antigen, the response of such individuals to the protein antigen is substantially diminished, with the provision that the at least one peptide does not comprise the entire protein antigen.

Bee Venom Allergens:

Bee venom (BV) is a complex mixture of antigens that can include one or more toxic polypeptides. Many of these polypeptides are hypersensitizing agents and can additionally have hemolytic or neurotoxic effects.

Approximately 3% of the general population are hypersensitive to BV polypeptides. IgE antibodies from BV hypersensitive individuals recognize several BV toxic polypeptides. BV polypeptides, often referred to as allergens, recognized by IgE in BV hypersensitive individuals can include, e.g., phospholipase $A_2$ ($PLA_2$), acid phosphatase, hyaluronidase, allergen C, and other, high molecular weight (MW) proteins.

BV hypersensitive individuals can be at high risk of an adverse reaction to a bee sting. One recognized method for preventing or minimizing serious adverse reactions resulting from a bee sting is to desensitize the individual to the allergens present in BV. This protection can be induced by a process termed venom immunotherapy (VIT).

Conventional VIT based on a standardized preparation of bee venom allergens provides complete protection in at least 80% of patients after a 3-5 year desensitization. (See Kämmerer et al., Clin. Experiment. Allergy. 27:1016-1026, 1997).

Birch Pollen Allergens:

Birch pollen is a major source of type I allergies observed in early spring. An estimated 100 million individuals suffer from birch pollen allergy. Cross-linking of two IgE receptors on the surface of mast cells and basophilic leucocytes, by allergen binding, initiates the release of a number of physiologically active substances such as histamine, PAF (platelet activating factor), heparin, chemotactic factors for eosinophilic and neutrophilic granulocytes, leucotrienes, prostaglandins and thromboxanes. It is these mediators which cause the direct symptoms of IgE-mediated allergic reactions (Type I hypersensitivity).

Bet v 1, the major birch pollen allergen, is composed of 160 amino acid residues with a molecular weight of approximately 17 kDa. To date, eleven Bet v 1 protein sequence isoforms have been identified, with amino acid identities ranging from 84.4% (25/160 amino acid exchanges) to 99.4% (a single amino acid exchange). (See, Swoboda et al., J. Biol. Chem. 270(6):2607. 1995). Major three-dimensional structural features of Bet v 1 include a seven-stranded antiparallel beta-sheet that wraps around a long C-terminal alpha-helix, thereby forming a large cavity in the interior of the protein.

Birch pollen profilin, Bet v 2, is composed of 133 amino acid residues with a molecular weight of approximately 15 kDa. It is a structurally well conserved actin- and phosphoinositide-binding protein and a cross-reactive allergen. Structural features include three α-helices and seven β-strands, as determined by NMR.

When peptides derived from birch pollen proteins or variants are used to tolerize an individual sensitive to a protein allergen, the peptide is preferably derived from a protein allergen of the genus *Betula verrucosa*. The immunogenic features of rBet v 1 fragments/variants have been shown. (See, Vrtala et al., J. Immunol. 165:6653, 2000; van Hage-Hamsten et al., J. Allergy Clin. Immunol. 104(5):969, 1999; Vrtala et al., Int. Arch Allergy Immun. 113:246, 1997; and Wiedermann et al., Int. Arch. Allergy Immun. 126:68 2001).

Dust Mite Allergens:

The dust mite (DM) is a common cause of allergic rhinitis and asthma. A dust mite is a microscopic, eight-legged insect. More than 100,000 dust mites can be in a single gram of dust. People are not allergic to the dust mite itself, but to dust mite feces. Dust mites eat the microscopic skin dander found on people and animals, and then leave droppings. Each dust mite can produce approximately 20 droppings each day. Dust mite are found on people, animals and on almost every surface in homes, including carpet, upholstered furniture, mattresses and box springs, sheets and blankets, pillows and stuffed animals. When dead dust mites and dust mite droppings become airborne and are inhaled, they may produce an allergic reaction.

Two species of the mite genus *Dermatophagoides*, *D. pteronyssinus* and *D. farinae*, are important sources of house dust allergens. Two groups of major allergens, Der 1 (Der p 1 and DER f 1) and Der 2 (Der p 2 and Der f 2), have been purified from these *Dermatophagoides* species.

Sequences and Corresponding SEQ ID Numbers:

The sequences and corresponding SEQ ID NOs discussed herein include the following:

SEQ ID NO:1 $PLA_2$ fragment amino acid sequence (60 aa)

SEQ ID NO:2 $PLA_2$ fragment amino acid sequence (53 aa)

SEQ ID NO:3 $PLA_2$ fragment amino acid sequence (45 aa)

SEQ ID NO:4 $PLA_2$ amino acid sequence (134 aa)

SEQ ID NO:5 Bet v 1 fragment amino acid sequence (90 aa)

SEQ ID NO:6 Bet v 1 fragment amino acid sequence (80 aa)

SEQ ID NO:7 Bet v 1 amino acid sequence (160 aa)

SEQ ID NO:8 Bet v 2 fragment amino acid sequence (70 aa)

SEQ ID NO:9 Bet v 2 fragment amino acid sequence (73 aa)

SEQ ID NO:10 Bet v 2 amino acid sequence (133 aa)

SEQ ID NO:11 Der p 1 fragment amino acid sequence (81 aa)

SEQ ID NO:12 Der p 1 fragment amino acid sequence (86 aa)

SEQ ID NO:13 Der p 1 fragment amino acid sequence (86 aa)

SEQ ID NO:14 Der p 1 amino acid sequence (212 aa)

SEQ ID NO:15 Der p 2 fragment amino acid sequence (73 aa)

SEQ ID NO:16 Der p 2 fragment amino acid sequence (73 aa)

SEQ ID NO:17 Der p 2 amino acid sequence (136 aa)

TABLE 1

Amino Acid Sequences of the Invention

| Amino Acid Sequence | SEQ ID NO |
|---|---|
| IIYPGTLWCGHGNKSSGPNELGRFKHTDACCR THDMCPDVMSAGESKHGLTNTASHTRLS | (SEQ ID NO: 1) |
| KHGLTNTASHTRLSCDCDDKFYDCLKNSADTI SSYFVGKMYFNLIDTKCYKLE | (SEQ ID NO: 2) |
| LIDTKCYKLEHPVTGCGERTEGRCLHYTVDKS KPKVYQWFDLRKY | (SEQ ID NO: 3) |
| IIYPGTLWCGHGNKSSGPNELGRFKHTDACCR THDMCPDVMSAGESKHGLTNTASHTRLSCDCD DKFYDCLKNSADTISSYFVGKMYFNLIDTKCY KLEHPVTGCGERTEGRCLHYTVDKSKPKVYQW FDLRKY | (SEQ ID NO: 4) |
| MGVFNYETEATSVIPAARLFKAFILDGDNLFP KVAPQAISSVENIEGNGGPGTIKKISFPEGFP FKYVKDRVDEVDHTNFKYNYSVIEGGHPVTGC GERTEGRCLHYTVDKSKPKVYQWFDLRKY | (SEQ ID NO: 5) |
| KYNYSVIEGGPIGDTLEKISNEIKIVATPDGG SILKISNKYHTKGDHEVKAEQVKASKEMGETL LRAVESYLLAHSDAYN | (SEQ ID NO: 6) |
| MGVFNYETEATSVIPAARLFKAFILDGDNLFP KVAPQAISSVENIEGNGGPGTIKKISFPEGFP FKYVKDRVDEVDHTNFKYNYSVIEGGPIGDTL EKISNEIKIVATPDGGSILKISNKYHTKGDHE VKAEQVKASKEMGETLLRAVESYLLAHSDAYN | (SEQ ID NO: 7) |
| MSWQTYVDEHLMSDIDGQASNSLASAIVGHDG SVWAQSSSFPQFKPQEITGIMKDFEEPGHLAP TGLHLG | (SEQ ID NO: 8) |
| HLAPTGLHLGGIKYMVIQGEAGAVIRGKKGSG GITIKKTGQALVFGIYEEPVTPGQSNMVVERL GDYLIDQGL | (SEQ ID NO: 9) |
| MSWQTYVDEHLMSDIDGQASNSLASAIVGHDG SVWAQSSSFPQFKPQEITGIMKDFEEPGHLAP TGLHLGGIKYMVIQGEAGAVIRGKKGSGGITI KKTGQALVFGIYEEPVTPGQSNMVVERLGDYL IDQGL | (SEQ ID NO: 10) |
| TNACSINGNAPAEIDLRQMRTVTPIRMQGGCG SCWAFSGVAATESAYLAYRNQSLDLAEQELVD CASQHGCHGDTIPRGIE | (SEQ ID NO: 11) |
| SQHGCHGDTIPRGIEYIQHNGVVQESYYRYVA REQSCRRPNAQRFGISNYCQIYPPNVNKIREA LAQTHSAIAVIIGIKDLDAFRH | (SEQ ID NO: 12) |
| AIAVIIGIKDLDAFRHYDGRTIIQRDNGYQPN YHAVNIVGYSNAQGVDYWIVRNSWDTNWGDNG YGYFAANIDLMMIEEYPYVVIL | (SEQ ID NO: 13) |
| TNACSINGNAPAEIDLRQMRTVTPIRMQGGCG SCWAFSGVAATESAYLAYRNQSLDLAEQELVD CASQHGCHGDTIPRGIEYIQHNGVVQESYYRY VAREQSCRRPNAQRFGISNYCQIYPPNVNKIR EALAQTHSAIAVIIGIKDLDAFRHYDGRTIIQ RDNGYQPNYHAVNIVGYSNAQGVDYWIVRNSW DTNWGDNGYGYFAANIDLMMIEEYPYVVIL | (SEQ ID NO: 14) |
| DQVDVKDCANHEIKKVLVPGCHGSEPCIIHRG KPFQLEAVFEANQNTKTAKIEIKASIDGLEVD VPGIDPNA | (SEQ ID NO: 15) |
| SIDGLEVDVPGIDPNACHYMKCPLVKGQQYDI KYTWNVPKIAPKSENVVVTVKVMGDDGVLACA IATHAKIRD | (SEQ ID NO: 16) |

TABLE 1-continued

Amino Acid Sequences of the Invention

| Amino Acid Sequence | SEQ ID NO |
|---|---|
| LVAAVARDQVDVKDCANHEIKKVLVPGCHGSE PCIIHRGKPFQLEAVFEANQNTKTAKIEIKAS IDGLEVDVPGIDPNACHYMKCPLVKGQQYDIK YTWNVPKIAPKSENVVVTVKVMGDDGVLACAI ATHAKIRD | (SEQ ID NO: 17) |

Chimeric Allergens

The present invention further provides compositions and kits for diagnostic use that are comprised of one or more containers containing a chimeric allergen protein and contiguous overlapping peptide fragments. The chimeric allergen protein and peptide fragments are comprised of peptide fragments from different allergens (e.g. one or more from allergen one with one or more from allergen two from the same class of allergen (e.g. bee venom, birch pollen, dust mite, etc.)). The kit may, optionally, further comprise a series of compositions of known concentration, a positive-control and a negative-control in the aforementioned assays.

In a preferred embodiment the chimeric protein comprises peptide fragments within a specified allergen class. For example, chimeric proteins comprising Bet v 1 (SEQ ID NO:5 and 6) and Bet v 2 (SEQ ID NO:8 and 9) peptide fragments or Der p 1 (SEQ ID NO:11-13) and Der p 2 (SEQ ID NO:15 and 16). These peptide fragments would be contiguous, however the fragments can be distant from each other and in various orientations and may include overlapping peptides.

For example, the schematic below shows an example of overlapping peptide fragments:
ABCDEF=OPF (1 fragment 1)
DEFGHI=OPF (1 fragment 2)
123456=OPF (2 fragment 1)
456789=OPF (2 fragment 2)
which can be used to generate overlapping chimeric peptide fragments, for example:
ABCDEF123456=OPF (Chimeric fragment 1)
456789DEFGHI=OPF (Chimeric fragment 2)
OR
123456ABCDEF=OPF (Chimeric fragment 3)
DEFGHI456789=OPF (Chimeric fragment 4)

In another embodiment, the chimeric protein comprises peptide fragments from different allergen classes. For example, chimeric proteins comprising PLA$_2$ (SEQ ID NO:1-3) and Bet v 1 (SEQ ID NO:5 and 6) or Bet v 2 (SEQ ID NO:8 and 9) peptide fragments or chimeric proteins comprising PLA$_2$ (SEQ ID NO:1-3) and Der p 1 (SEQ ID NO:11-13) or Der p 2 (SEQ ID NO:15 and 16). Chimeric peptide fragments from different allergens are useful in diagnosing patients with different allergies. For example, chimeric proteins comprising PLA$_2$ and Bet v 1 or Bet v 2 would be applicable to patients allergic to both bee venom and birch pollen.

Any chimeric protein, or fragment or combinations thereof, comprising SEQ ID NOs: 1-3, 5, 6, 8, 9, 11-13, 15 and 16 is included in the present invention. Preferred chimeric peptide fragments are listed in Table 2. For example, SEQ ID NO:18 comprises (in linear arrangement) SEQ ID NOs:5 and 8; SEQ ID NO:19 comprises SEQ ID NOs:9 and 6; SEQ ID NO:20 comprises SEQ ID NOs:8 and 5; SEQ ID NO:21 comprises SEQ ID NOs:6 and 9; SEQ ID NO:22 comprises SEQ ID NOs:15 and 11 and SEQ ID NO:23 comprises SEQ ID NOs:13 and 16.

TABLE 2

CHIMERIC AMINO ACID SEQUENCES

| Amino Acid Sequence | SEQ ID NO |
|---|---|
| MGVFNYETEATSVIPAARLFKAFILDGDNLFP KVAPQAISSVENIEGNGGPGTIKKISFPEGFP FKYVKDRVDEVDHTNFKYNYSVIEGGMSWQTY VDEHLMSDIDGQASNSLASAIVGHDGSVWAQS SSFPQFKPQEITGIMKDFEEPGHLAPTGLHLG | (SEQ ID NO: 18) |
| HLAPTGLHLGGIKYMVIQGEAGAVIRGKKGSG GITIKKTGQALVFGIYEEPVTPGQSNMVVERL GDYLIDQGLKYNYSVIEGGPIGDTLEKISNEI KIVATPDGGSILKISNKYHTKGDHEVKAEQVK ASKEMGETLLRAVESYLLAHSDAYN | (SEQ ID NO: 19) |
| MSWQTYVDEHLMSDIDGQASNSLASAIVGHDG SVWAQSSSFPQFKPQEITGIMKDFEEPGHLAP TGLHLGMGVFNYETEATSVIPAARLFKAFILD GDNLFPKVAPQAISSVENIEGNGGPGTIKKIS FPEGFPFKYVKDRVDEVDHTNFKYNYSVIEGG | (SEQ ID NO: 20) |
| KYNYSVIEGGPIGDTLEKISNEIKIVATPDGG SILKISNKYHTKGDHEVKAEQVKASKEMGETL LRAVESYLLAHSDAYNHLAPTGLHLGGIKYMV IQGEAGAVIRGKKGSGGITIKKTGQALVFGIY EEPVTPGQSNMVVERLGDYLIDQGL | (SEQ ID NO: 21) |
| DQVDVKDCANHEIKKVLVPGCHGSEPCIIHRG KPFQLEAVFEANQNTKTAKIEIKASIDGLEVD VPGIDPNATNACSINGNAPAEIDLRQMRTVTP IRMQGGCGSCWAFSGVAATESAYLAYRNQSLD LAEQELVDCASQHGCHGDTIPRGIE | (SEQ ID NO: 22) |
| AIAVIIGIKDLDAFRHYDGRTIIQRDNGYQPN YHAVNIVGYSNAQGVDYWIVRNSWDTNWGDNG YGYFAANIDLMMIEEYPYVVILSIDGLEVDVP GIDPNACHYMKCPLVKGQQYDIKYTWNVPKIA PKSENVVVTVKVMGDDGVLACAIATHAKIRD | (SEQ ID NO: 23) |

Kits Including Allergens

The present invention additionally provides kits for diagnostic use that are comprised of one or more containers containing a specific allergen protein and contiguous overlapping peptide fragments. The kit may, optionally, further comprise a series of compositions of known concentration, a positive-control and a negative-control in the aforementioned assays.

Allergies to various allergens can be treated with the compositions and methods of the invention. Examples of allergens include, but are not limited to:

The following Examples are presented in order to more fully illustrate the preferred embodiments of the invention. These Examples should in no way be construed as limiting the scope of the invention, as defined by the appended claims.

EXAMPLES

Example 1

Bee Venom Specific T Cell Tolerance Induction with Allergen-Derived Overlapping Peptide Fragments This study was designed to evaluate the safety and immunogenicity of an allergen-derived overlapping peptide fragment (OPF) immunotherapy.

Materials and Methods

Patients: Sixteen bee venom (BV) hypersensitive patients were recruited from the Outpatient Clinic of the Division of Allergy and Immunology, Lausanne, Switzerland (9 males/7 females). Criteria for enrollment were grade I to IV systemic hypersensitivity reaction to honey bee field sting (Müller J. Asthma Res. 3:331-333, 1996); positive anti-$PLA_2$ and anti-whole BV specific IgE (>0.35 kU/l as titrated by CAP system, Pharmacia, Uppsala, Sweden, and by immunoblotting), positive immediate intradermal (ID) skin tests to phospholipase $A_2$ ($PLA_2$) and whole BV (presence of a wheal >5 mm with erythema at an allergen concentration ≤0.1 µg/ml) and negative ID test to individual OPF and OPF mixture (≤5 mm wheal and flare reaction at peptide concentration >0.1 µg/ml).

Peptide synthesis and purification: Three overlapping peptide fragments $OPF_{1-60}$ (SEQ ID NO:1), $OPF_{47-99}$ (SEQ ID NO:2) and $OPF_{90-134}$ (SEQ ID NO:3) mapping the entire 134 amino acids of $PLA_2$ (SEQ ID NO: 4) from *Apis mellifera* were synthesized on an Applied Biosystems 431A Peptide Synthesizer (Perkin Elmer, Foster City, Calif.) and purified as described in Roggero et al., FEBS Lett. 408:285-288, 1997. Analytical HPLC and mass spectrometry were used to assess the purity of each peptide (>80%), which were readily soluble in PBS. On the day of injection, the peptide mixture was reconstituted in an 0.3 mg/ml albumin solution (containing 4 mg/ml of phenol) (ALK/Abello, Horsholm, Denmark) and injected subcutaneously in the deltoid area.

Skin testing: ID tests with BV, $PLA_2$ and peptides were performed as described in Müller et al., Allergy 48(14):37-46, 1993. Concentrations tested ranged from $10^{-3}$ µg/ml to 1 µg/ml (10-fold dilution series). An ID test result was considered positive when a wheal reaction superior to 5 mm (for BV, $PLA_2$ and peptides) in diameter and an erythema were present at a concentration ≤0.1 µg/ml. The 0.1 µg/ml concentration was defined as the end-point concentration (EPC), as higher concentrations of BV and $PLA_2$ may induce non specific toxic reactions. See Müller et al., J. Allergy Clin. Immunol. 96:395-402, 1995.

Study design: The study was designed as a double blind, randomized, two-dose, placebo-controlled trial. At day 0, patients (n=9) from the OPF group were injected at 30 min interval with successively 0.1 µg, 1 µg, 10 µg, 20 µg, 40 µg, 80 µg and 100 µg of each of the three OPFs (cumulative dose of 251.1 µg of each OPF within 3 h). Seven patients were then injected at day 4, 7, 14, 42 and 70 with a maintenance dose of 100 µg of each of the three OPFs. A maintenance dose of 300 µg of each OPF was initially injected to two patients up to day 42. Patients from the control group (n=7) were injected with an equivalent volume of peptide diluent only (0.3 mg/ml albumin solution, containing 4 mg/ml of phenol) (ALK/Abello, Horsholm, Denmark).

Reagents: Whole BV and $PLA_2$ were purchased from Latoxan (Rosans, France). For cell culture, $PLA_2$ was further purified by HPLC. Its cytotoxicity was inhibited by overnight reduction at 37° C. with a 100 molar excess of dithiothreitol, followed by alkylation with a 1000 molar excess of N-ethylmaleimide. $PLA_2$ was finally purified on a Sephadex G-25 column (Pharmacia, Uppsala, Sweden). PMA and ionomycin were purchased from Calbiochem, San Diego, Calif.

Proliferation assays: Blood was drawn immediately before each OPF injection and peripheral blood mononuclear cells (PBMC) were isolated from heparinized blood by density gradient centrifugation over Ficoll-Paque (Pharmacia Biotech AB, Uppsala, Sweden). Prior to $^3$H-thymidine (Du Pont NEN Products Boston, Mass., USA) incorporation, PBMC ($2\times10^5$/well) from each donor were cultured for 6 days in octoplicates in 96 well flat bottom plates (Costar Corning Inc., New York, N.Y.) in RPMI 1640 medium (Gibco, Basel, Switzerland) containing 10% AB$^+$ serum (Swiss Red Cross, Bern, Switzerland), 2 mM glutamine, 1% Na-pyruvate, 1% non-essential amino acids, 1% kanamycine (all from Gibco) with optimal concentration of OPFs (10 µg/ml) or PLA$_2$ (10 µg/ml). See Kämmerer et al., J. Allergy Clin. Immunol. 100:96-103, 1997.

Short term T cell lines: T cell lines were derived from PBMC that were isolated before each injection and stimulated in 24 well plates (Nunc) ($10^6$ cells/well) with a mixture of the three OPFs (10 µg/ml) for 7 days in supplemented 10% AB$^+$RPMI 1640 medium as described above. The short term T cell lines obtained were washed and restimulated for 24 h (for IL-4, IL-5, IL-13 and TGFβ secretion) or 48 h (for IFNγ and IL-10) with plastic crosslinked OKT3 (1 µg/ml) (see Jutel et al., Clin. Experiment. Allergy 25:1108-1117, 1995). Cell culture supernatants were collected for cytokine quantification and stored at −80° C.

Cytokine quantification: IL-4, IL-10 and IFNγ were titrated using commercially available ELISA kits (Mabtech AG, Nacka, Sweden, for IL-4, IL-10 and IFNγ☐☐ and R&DSystem for IL-5, IL-13 and TGFβ), according to manufacturer's recommendations.

Quantification of specific serum IgE and IgG$_4$: Whole BV and anti-PLA$_2$ specific IgE were quantified using the Phamarcia CAP System Fluoroimmunoassay (Pharmacia Diagnostic AB, Uppsala, Sweden) as described in Kämmerer et al., J. Allergy Clin. Immunol. 100:96-103, 1997. For quantification of specific anti-PLA$_2$ IgG4, native PLA$_2$ (5 µg/ml) was coated on 96 well plates (Maxisorb, Denmark) in carbonate/bicarbonate buffer pH 9.6, for 2 h at room temperature. Plates were blocked with milk 5%/PBS/Tween 0.05%. Serial dilutions of sera in 1% milk/Tween 0.05% were incubated for 1 h at room temperature. Plates were washed thrice, incubated with horseradish peroxidase labeled anti-IgG4 mAb JDC-14 ¹⁄₁₀,₀₀₀ (Pharmingen, Hamburg, Germany), and revealed in 3,3',5,5'-tetramethylbenzidine (TMB). Optical density was determined at 450 nm on a microtiter plate analyzer (MR5000, Dynatech Laboratories). Titers were reported to a standard serum and expressed as arbitrary standard units.

Immunoblotting and dot blot analysis: Anti-BV or -PLA$_2$ immunoblots were processed as described in Kettner et al., Clin. Experiment. Allergy 29:394-401, 1999. For dot blot analysis, 1 µg of whole BV, PLA$_2$, OPFs or human albumin was diluted ¼ in DMSO, spotted on PVDF membranes and dried for 30 min. at 37° C. After blocking in non-fat milk 5%, further steps were performed as described in Kettner et al., Clin. Experiment. Allergy 29:394-401 1999. Dot densities were analyzed by scanning densitometry using an Advanced American Biotechnology scanner, Fullerton, Calif.

Statistical analysis: Differences within and between groups were evaluated by non-parametric ANOVA tests (Friedman or Kruskal-Wallis non parametric test with multicomparison post-test, or Mann-Whitney test respectively); or by Fisher's exact test (between group differences: responders versus non-responders, positive responses being defined as a doubling of day 0 value), using an Instat 3.0 software.

Results

Patients' data: Patients were randomly assigned to the OPF or control (albumin) groups. In the OPF group, mean age of patients was 39±14 yrs (5 males/4 females). One patient had a previous history of grade I hypersensitivity to BV, 7 a grade III and one a grade IV according to Mueller's classification. EPC for ID tests to BV was $10^{-1.7}$ µg/ml (geometric mean). Mean serum anti-BV specific IgE level was 21.5±33.9 kU/l. In the control group, mean age was 40±10 yrs (4 males/3 females). One patient had previously developed a grade I hypersensitivity reaction to bee venom, three a grade II and three a grade III. EPC for ID tests to BV was $10^{-2.0}$ µg/ml (geometric mean). Mean serum anti-BV specific IgE level was 29.8±26.1 kU/l. There was no significant difference between groups at inclusion regarding sex, ages, severity of initial clinical reaction, anti-BV IgE and anti-PLA$_2$ specific IgE and IgG4 antibody levels.

Overlapping peptide immunotherapy induces T cell anergy: In both groups, PBMC collected before each OPF or albumin injection were stimulated with the three OPF mixture (10 µg/ml). As reported in Kämmerer et al., J. Allergy Clin. Immunol. 100:96-103, 1997, T cell proliferation in response to the three OPFs (expressed as the ratio of T cell response to PMA (100 ng/ml)/Ionomycine (1 µM) used as internal control) before the first injection at day 0 was low in either group all along the study, and persisted so in the control group (Friedman, p>0.05) (FIG. 1). In contrast, there was a marked enhancement of T cell proliferation ratio in response to the three OPFs in the peptide group, which was significant both within (Friedman, p=0.035) and between groups (Mann-Whitney, day 14 and day 42, p<0.05). Proliferation ratio median rose from 0.03 to 0.22 at day 14 to progressively decrease thereafter to those obtained in the control group, demonstrating an active tolerance induction. This pattern thus demonstrated that T cell tolerance occurring after day 42 in the peptide group was preceded by a vigorous activation phase peaking at day 14.

Figure 2:
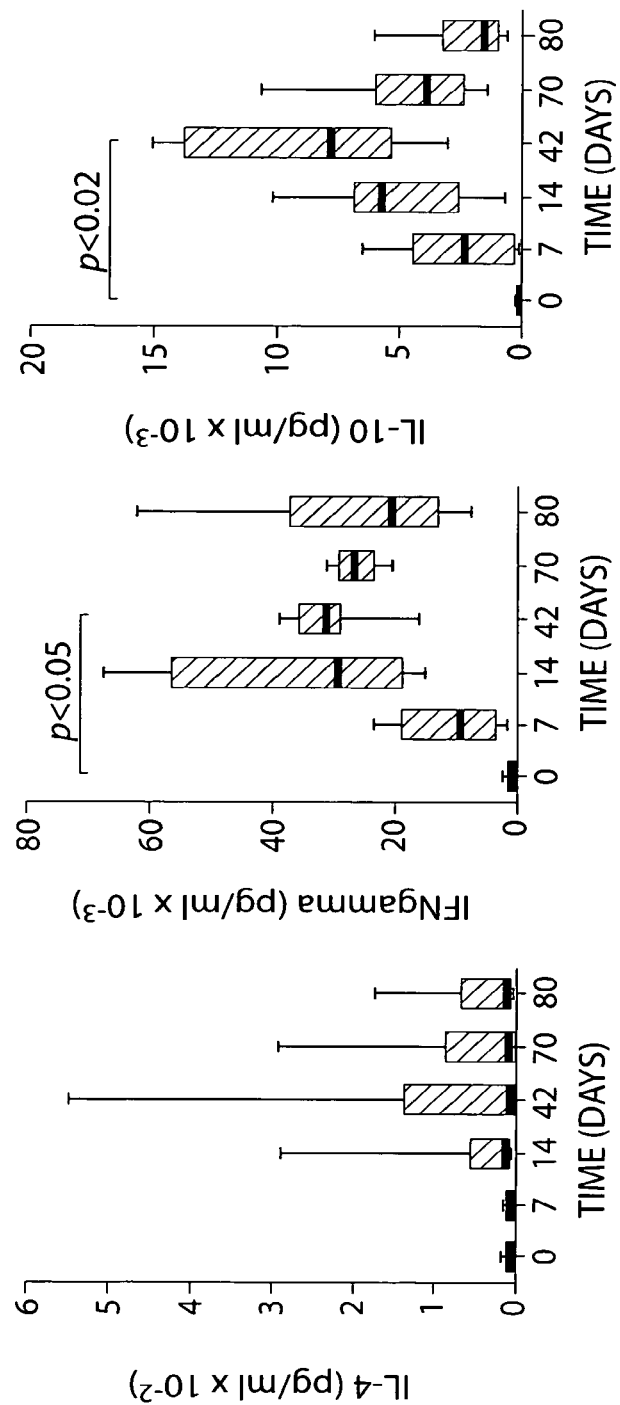
FIGS. 2A, 2B and 2C depict is a series of graphs showing overlapping peptide therapy deviates T cell cytokine response and strongly stimulates IL-10 secretion. Cytokines (FIG. 2A: IL-4.

T cell cytokine production: PBMC collected before each injection were stimulated with a mixture of the three OPFs for 7 days, then activated with OKT3 (1 µg/ml) for 24 to 48 hr, following previously described protocols (Jutel et al., Clin. Experiment Allergy 25:1108-1117, 1995). IL-4 secretion by PBMCs maximally stimulated with OKT3 remained low in the peptide group (FIG. 2A). A similar pattern was observed for IL-5 and IL-13 secretion. In contrast, we observed a striking enhancement of both IFNγ and IL-10 secretion by OPF specific T cells, which reached a peak at day 42 of therapy (Kruskal-Wallis, p<0.018 and <0.012 respectively) (FIG. 2B, 2C). IL-10 and IFNγ secretion tended to decline towards day 80 (non-significant). TGFβ secretion stayed at background level all along the trial. There was in contrast no change overtime in IL-4, IL-5, IL-10, IL-13, TGFβ and IFNγ production by PBMCs isolated from the control group. These data were compatible with a TH0 to TH1 immune deviation paralleled by an enhanced production of IL-10, a cytokine that may be involved in the active T cell tolerance induction observed (FIG. 1). See Akdis et al., J. Clin. Invest. 102:98-106, 1998.

Figure 3:
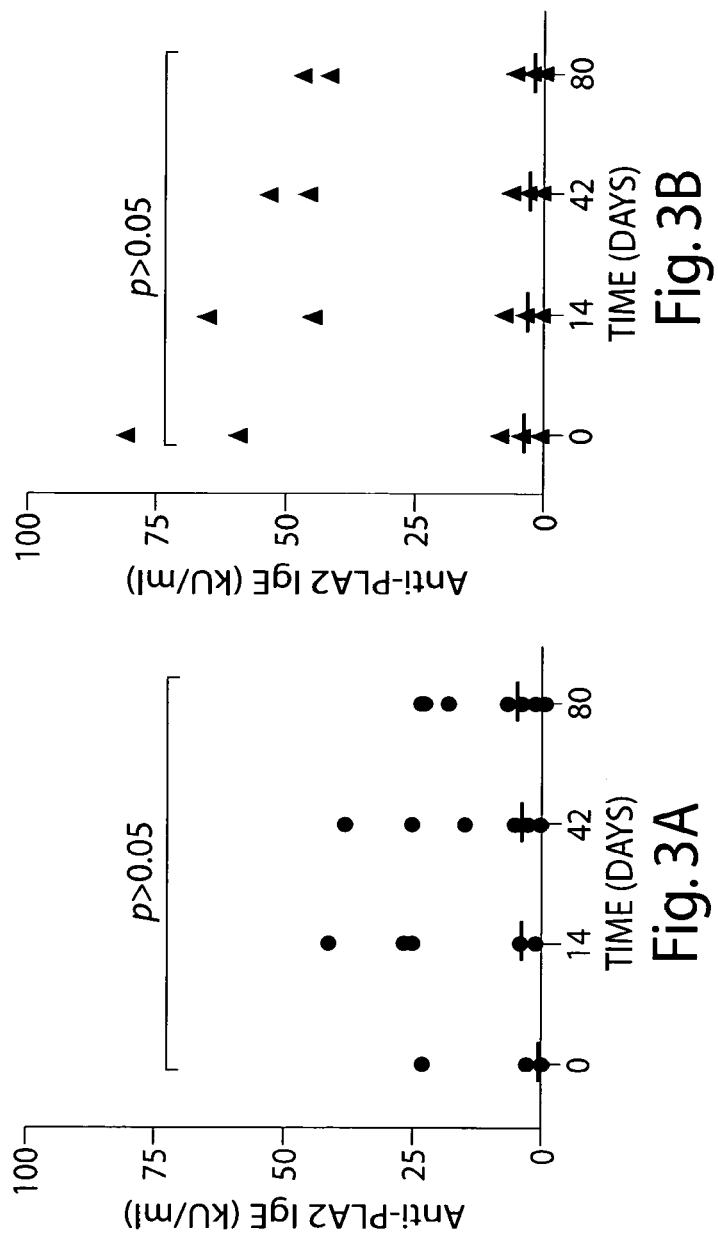
FIGS. 3A and 3B depict a series of graphs showing anti-$PLA_2$ specific serum IgE. Anti-$PLA_2$ specific serum IgE were measured in peptide-treated group (FIG. 3A) and in control group (FIG. 3B) at the indicated time-points. Median values are indicated by thick bars.
Figure 4:
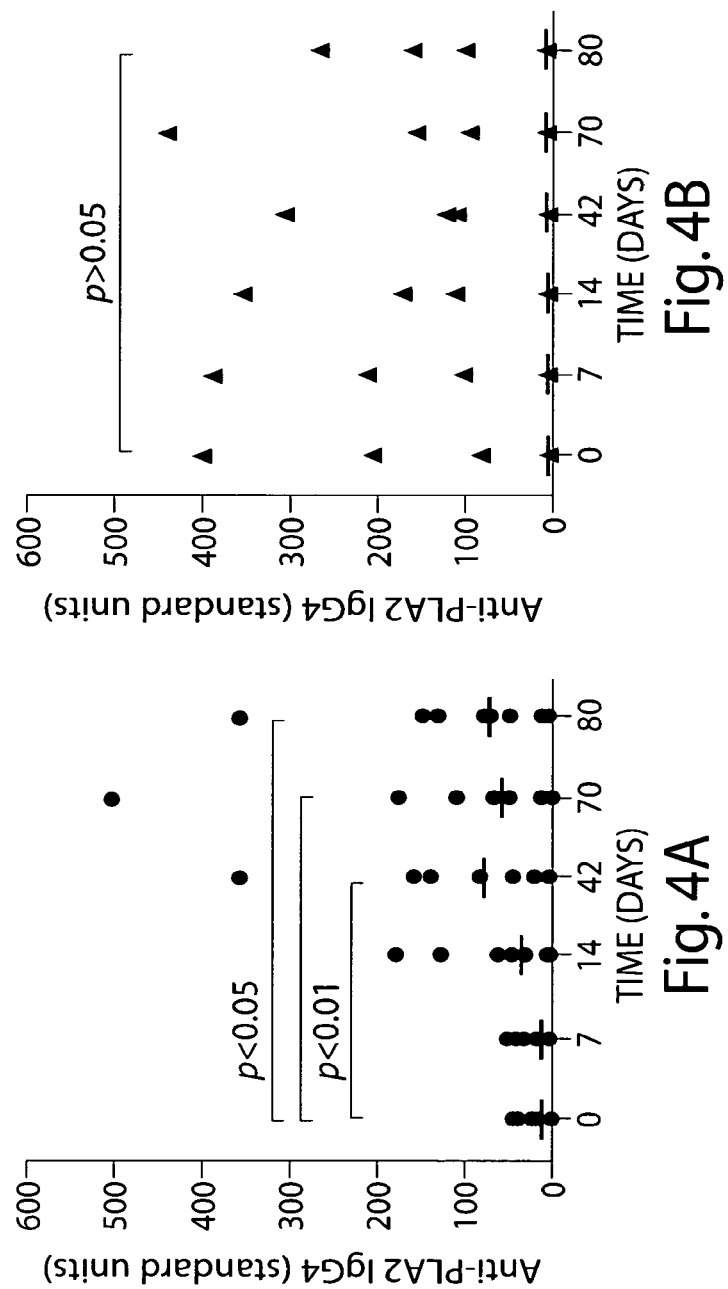
FIGS. 4A and 4B depict a series of graphs showing anti-PLA2.specific serum IgG4. Anti-PLA2 specific serum IgG4 were measured in peptide-treated group (FIG. 4A) and in control group (FIG. 4B) at the indicated time-points. Median values are indicated by thick bars.

Specific anti-PLA2 serum IgE and IgG$_4$: Serum anti-PLA$_2$ IgE were measured at screening visit, at days 14, 42 and 80 using a CAP assay. Though the difference between the anti-PLA$_2$ IgE levels overtime in the peptide versus the control group indicated a trend towards higher IgE value in the peptide group (Fisher's exact test, T14, T42, T80, p<0.03), comparison within the groups showed that there was no significant variation of anti-PLA2 IgE levels overtime (Friedman, p>0.05) (FIG. 3A, B). In contrast, specific anti-PLA$_2$ IgG4 antibodies steadily increased overtime within the peptide group to reach significance (Friedman, p<0.001) (FIG. 4A). Each point represents an individual value. Differences within the groups was statistically non-significant (Friedman p>0.05). Serum anti-PLA$_2$ IgG4 levels in the control group (FIG. 4B) remained constant all over the study and significantly differed from the peptide group (Fisher's exact test, T42, T70, T80, p<0.01).

Figure 5:
FIG. 5 is a photograph showing absence of immediate allergic reaction to overlapping peptide fragments. A representative patient from the peptide group was injected intradermally with, respectively from left to right, 0.01 µg/ml native $PLA_2$, 1 µg/ml of each of the three synthetic peptide fragments $OPF_{1-60}$, $OPF_{47-99}$ and $OPF_{90-134}$ separately and with a mixture of them (1 µg/ml each) (arrows).
Figure 6A:
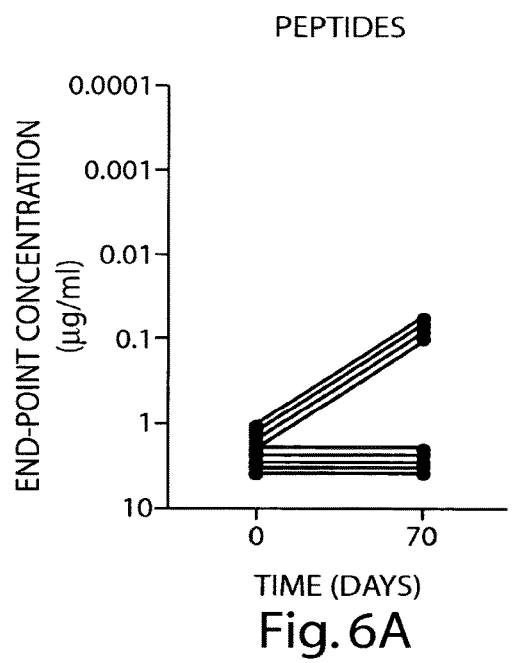
FIGS. 6A, 6B, 6C and 6D are a series of graphs showing intradermal skin tests with peptides and native $PLA_2$. Results are expressed as end-point concentrations ($log_{10}$ scale) at enrollment into the study (day 0) and after the last injection at day 70 in patients from peptide group (FIGS. 6A and 6B) and control group (FIGS. 6C and 6D), tested respectively with the three overlapping peptide fragments (as a mixture) (FIGS. 6A and 6C) and with native $PLA_2$ (FIG. 6B and FIG. 6D).
Figure 6B:
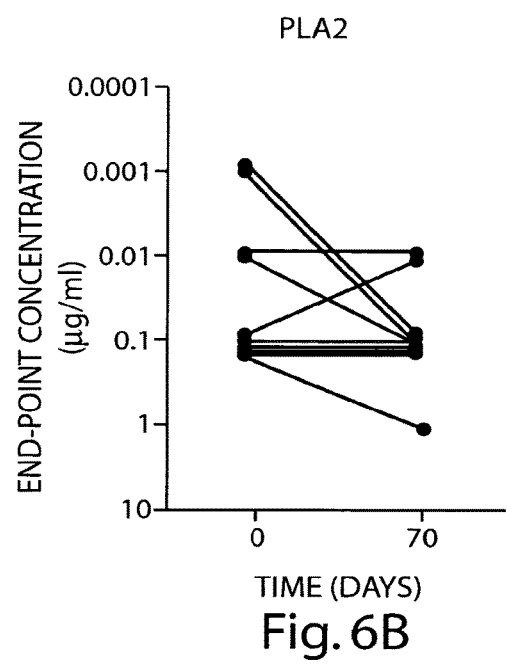
Figure 6C:
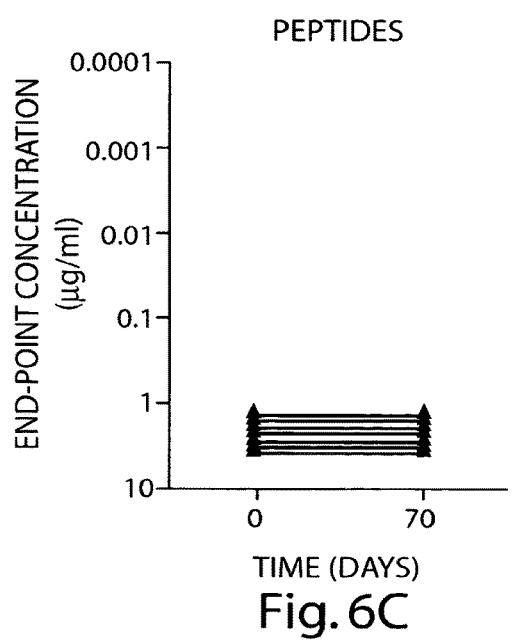
Figure 6D:
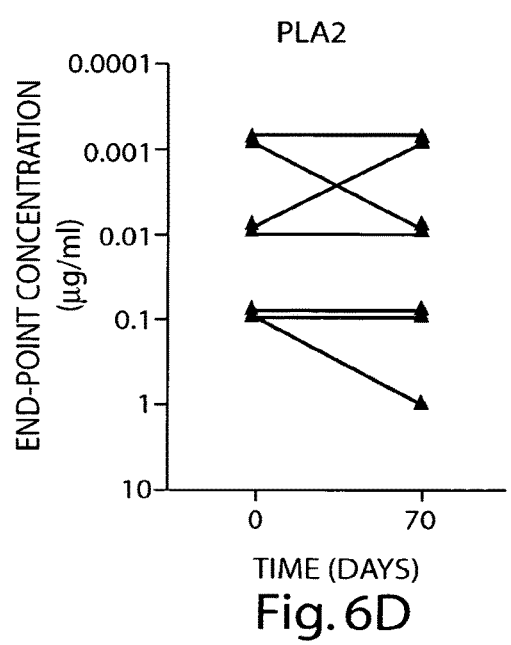

Skin immediate reactivity to intradermal tests: At the screening visit, none of the patients in the OPF or in the control group developed an immediate allergic reaction to intradermal injection of any of the three OPFs separately or as a mixture (EPC≥1 μg/ml) (FIG. 5 and FIGS. 6A, 6C). Each point represents an individual value. Differences within groups were examined by Friedmann non-parametric ANOVA test (p<0.001 for peptide group, p>0.05 for control group), completed in FIG. 6A by a multicomparison posttest (p<0.01, p<0.05 and p<0.05 for day 0 vs day 42, 70 and 80 respectively). At the end of the trial (day 70), none of the patients from the control group had EPC ≤0.1 μg/ml, whereas four out of the nine patients from the peptide group developed skin reactivity to the OPF mixture at 0.1 μg/ml, considered as the lower limit of positivity. At day 0, all patients in the OPF and control group had positive ID tests to native $PLA_2$ (FIG. 6B, 6D). At the end of the trial (day 70), in the peptide group (FIG. 6B), two patients increased their EPC by two log 10, and two others by one log 10. A single patient decreased his EPC to $PLA_2$ from 0.1 to 0.01 μg/ml, whereas four patients did not change their EPC to $PLA_2$. In the control group at day 70 (FIG. 6B), two patients increased their EPC to $PLA_2$ by one log, one patient decreased his EPC by one log and four did not modify their EPC. Though globally those changes were non significant between the groups, the only two patients who markedly enhanced their EPC to native $PLA_2$ (by two logs) were issued from the OPF group.

Figure 7A:
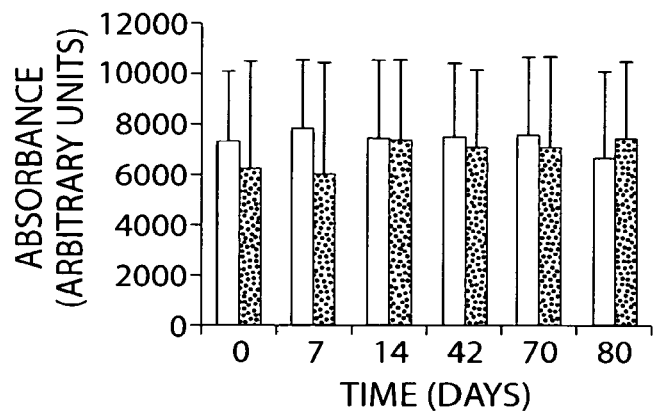
FIGS. 7A, 7B and 7C are a series of graphs showing in vitro IgE binding to whole BV and native $PLA_2$ (FIGS. 7A and 7B) and to overlapping peptide fragments $OPF_{1-60}$, $OPF_{47-99}$ and $OPF_{90-134}$ (FIGS. 7C, 7D, and 7E respectively), analyzed by dot blot assays after each injection. Results are expressed as absorbance arbitrary units. Open columns: control group; hatched columns: peptide group.
Figure 7B:
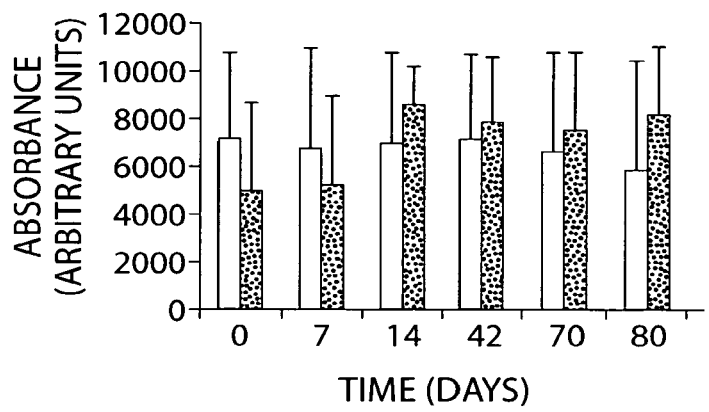
Figure 7C:
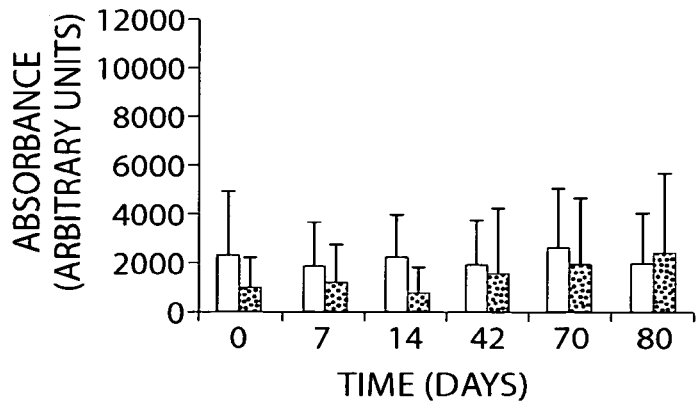
Figure 7D:
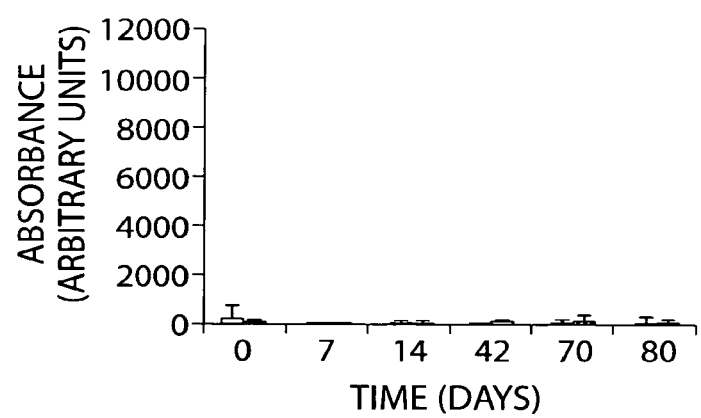
Figure 7E:
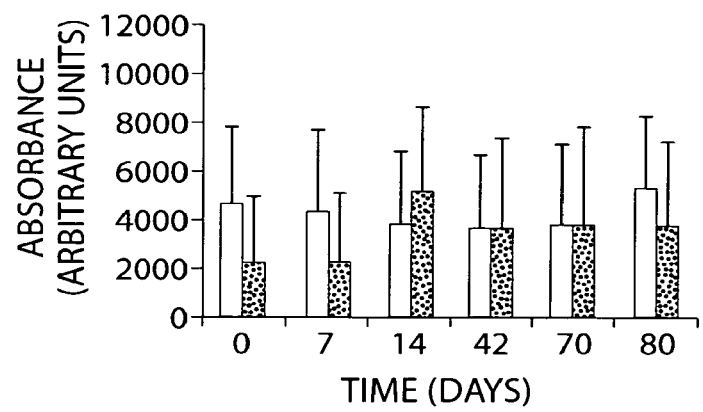

In vitro IgE binding to overlapping peptide fragments: In vitro specific IgE response to BV, native $PLA_2$ and each of the three OPFs was tested by dot assays at days 0, 7, 14, 42, 70 and 80 (FIG. 7). Though there was a trend to a modestly enhanced mean anti-whole BV and anti-native $PLA_2$ IgE binding in the peptide group at day 14 and later, as compared to days 0 and 7, there were no significant difference within and between the groups (FIGS. 7A, 7B). Similarly, there were no differences in IgE binding to individual OPF within and between the groups (FIG. 7C, 7D, 7E). Again, a non-significant trend towards enhanced IgE recognition of peptide $OPF_{90-134}$ was noted in the OPF group. Both in the control and peptide groups, the C-terminal peptide $OPF_{90-134}$ was binding IgE at a higher level followed by the N-terminal peptide $OPF_{1-60}$. IgE binding to the internal peptide $OPF_{47-99}$ was undetectable. Intradermal test with native $PLA_2$ only was positive.

Safety evaluation study: At day 0, despite the injection of sharply increasing OPF doses up to a cumulative dose of 250 μg of each peptide within 3.5 hrs (100 μg OPF group), none of the patients experienced local or systemic reactions. In two patients, mild, late (>2 hrs) local reactions (erythema) occurred after peptide injection at day 14, 42 and 70 to vanish after about an hour. In those two patients, after the last injection at day 70, hand palm pruritus and transient erythema of the upper part of the trunk occurred more than 3 h after OPF injection. There were no severe adverse events (life threatening reactions).

A maintenance dose of 300 μg OPF was initially injected to two patients. In one patient, the late occurrence (>2 hrs) of local skin reaction and upper trunk flush at day 42 led to the interruption of the treatment. The other patient, for safety reasons, was subsequently allocated to the 100 μg OPF treatment group, though the 300 μg dosage was well tolerated.

Discussion

This study showed that a peptide based allergen immunotherapy using OPFs derived from $PLA_2$, a major BV allergen, was able to induce T cell anergy, immune deviation toward a Th1 type T cell cytokine response, enhanced IL-10 secretion and $PLA_2$ specific IgG4 production. OPF immunotherapy was safe and did not induce severe systemic reactions though dose cumulation appeared to induce mild, non-immediate reactions in two patients.

The fact that OPFs could be injected without any local or systemic adverse events at day 0, though cumulative doses of each peptide were reaching more than 250 μg (550 μg in the two patients injected with 300 μg OPFs) demonstrates the high safety profile of OPFs. Mild local reactions (pruritus and erythema) occurred in only two patients at day 14, 42 and 70 more than 120 min. after the injection and did not last for more than one hour. In the same patients, the ultimate peptide injection led to late (>3 h) systemic reactions characterized by hand pruritus and a flash of the upper trunk. This presentation is not typical of anaphylaxis, since it occurred relatively late (>3 hrs) as compared to usual anaphylactic reactions during conventional immunotherapy or rush protocols that are triggered within minutes. The delayed character of these reactions were suggestive of a late allergic reaction, as interpreted in previous allergen peptide trials (Norman et al., Am. J. Respir. Crit. Care Med. 154: 1623-1628, 1996; Oldfield et al., J. Immunol. 167:1734-1739, 2001; and Haselden et al., J. Exp. Med. 189:1885-1894, 1999) and may be related to the stimulation of specific T cells to produce TH1 pro-inflammatory cytokines. These secondary events are dose-dependent (Oldfield et al., J. Immunol. 167:1734-1739, 2001), what certainly suggests a need to adapt the dose of OPFs in further clinical evaluations of OPF immunotherapy. Reactions were however all benign and self-limited. No life-threatening reactions occurred.

In vitro dot blot assays, a non-significant trend toward an enhanced IgE binding to native $PLA_2$, whole BV or peptides was apparent after the third OPF injection. Taken together with the trend in serum anti-$PLA_2$ IgE level increase, these data suggest that in OPF immunotherapy, as in conventional BV immunotherapy, an increase in allergen specific IgE may occur during the first weeks of treatment (Kämmerer et al., J. Allergy Clin. Immunol. 100:96-103, 1995 and Müller Insect Sting Allergy: clinical picture, diagnosis and treatment. Stuggart, New York: Gustav Fischer Verlag, 1990). This increase may essentially reflect the transient specific T cell activation observed during the first two weeks of therapy. IgE binding activity to peptides was clearly limited and plateaued after day 42. It was not reflected by in vivo skin testing at initiation of the study. During the course of the trial, four patients developed mildly positive ID tests to OPFs at 0.1 μg/ml, whereas the five others were still negative at 1 μg/ml. This difference was certainly significant since in the control group none of the patients had positive ID tests at 0.1 μg/ml concentration at the end of the trial. The clinical significance of these positive ID tests is however difficult to appreciate: the two patients who developed mild systemic reactions after day 70 injection were among those four patients. However, clinical tolerance to OPF injection was good in the two others. Longer term studies on larger study population will be necessary to assess the long term safety of OPF-based immunotherapy.

One of the most prominent results of this study was the induction of a profound specific T cell hyporesponsiveness at day 80. If at the screening visit, T cell proliferation in response to OPFs was low, what essentially suggested a low number of BV specific T cell precursors, it peaked at day 14 in the peptide group before progressing to hyporesponsiveness. Although previously shown in murine models (Tsitoura et al., J. Immunol. 163:2592-2600, 1999; Hoyne et al., Int. Immunol. 8:335-342 1996; and Pape et al., J. Immunol. 160:4719-4729, 1998), these results demonstrate in humans that anergy induction was preceded by T cell activation. This observation is in agreement with the recent demonstration that the late asthmatic reaction induced by the first administration of allergen-derived T cell peptides in cat allergic asthmatics preceded the induction of antigen-hyporesponsiveness (Oldfield et al., J. Immunol. 167:1734-1739, 2001. The progressive down-regulation of T cell response to OPFs was paralleled by enhanced IL-10 and IFN-γ secretion, peaking at day 42 to decrease thereafter. The pattern of T cell proliferation overtime was suggestive of T cell anergy induction. T cell clonal deletion may have also contributed to the phenomenon, especially with regard to the decrease in cytokine secretion occurring late in the course of therapy. Interestingly, the peak of IL-10 and IFNγ secretion occurred about 4 weeks after the maximal T cell proliferation, i.e. at a time when T cell anergy was established. This situation is not incompatible with T cell tolerance, since in vitro anergic $CD4^+$ T cell clones are still able to differentiate into Th1-like effector cells, to participate in T-dependent IgG2a anti-hapten responses and delayed-type hypersensitivity reactions (Malvey et al., J. Immunol. 161:2168-2177, 1998. Similarly, in allergy models to $PLA_2$ in mice, a persistence of a strong IFNγ production and anti-allergen IgG2a response despite tolerance induction by OPFs was shown (von Gamier et al., Eur. J. Immunol 30:1638-1645, 2000 and Astori et al., J. Immunol. 165:3497-3505, 2000). IL-10 has been involved in T cell anergy induction and appeared to be secreted by a sub-population of T lymphocytes able to repress other $CD4^+$ T cell specific activity, the so-called Tr1 subset (Groux et al., Nature 389:737-742, 1997 and Akdis et al., FASEB J. 13:603-609, 1999). IL-10 has also prominent anti-inflammatory properties (de Waal Malefyt et al., J. Immunol. 150:4754-4765, 1993). Though by itself an immune deviation to a TH1 type cytokine production may be deleterious (Hansen et al., J. Clin. Invest. 103:175-183, 1999), a combination of an anti-inflammatory cytokine such as IL-10 and IFNγ may re-equilibrate a potentially detrimental cytokine secretion.

Specific anti-$PLA_2$ serum IgG4 response was significantly stimulated. Previously, a gradual rise in IgG4 during the incremental phase of conventional immunotherapy has been demonstrated (Kämmerer et al., J. Allergy Clin. Immunol. 100:96-103, 1997 and Müller et al., Allergy 44:412-418, 1989). Serum IgG4 levels may be predictive of effective protection in response to immunotherapy (Urbanek et al., Clin. Allergy 16:317-322, 1986 and Lesourd et al., J. Allergy Clin Immunol. 83:563-571, 1989), though this concept may be controversial (Müller et al., Allergy 44:412-418, 1989). It was recently shown that IgE and IgG4 levels obtained after 2 years of specific immunotherapy were specific and sensitive predictors of reactivity post hymenoptera venom challenge, a high IgG4 response being associated with protection and low IgG4 levels with anaphylaxis (011ert et al., J. Allergy Clin. Immunol. 105:S59, Abstract 178, 2000). IgG4 may in part compete with IgE binding on allergen and thus contribute to clinical protection (Schneider et al., J. Allergy Clin. Immunol 94:61-70, 1994).

This placebo-controlled trial demonstrated that an OPF-based allergen immunotherapy was safe and able to induce specific T cell hyporesponsiveness, immune deviation toward TH1 cytokine secretion with parallel IL-10 secretion, and enhanced IgG4 production. As such, OPF immunotherapy reproduces the pattern of cellular and humoral events observed in rush and conventional immunotherapy without their inherent anaphylactic secondary events (Kämmerer et al., J. Allergy Clin. Immunol. 100:96-103, 1997; Akdis et al., J. Clim. Invest. 102:98-106, 1998; Akdis et al., J Clin Invest 98:1676-83, 1996; and Jutel et al., J. Immunol. 154:4187-4194, 1995).

Example 2

Birch Pollen (Bet v 1) Specific T Cell Tolerance Induction with Allergen-Derived Overlapping Peptide Fragments Materials and Methods Patients: Patients eligible for this study include those with a history of seasonal birch pollen allergy and with an SPT reaction 3+ compared with an albumin 10 mg/mL wheal and a minimal outcome of more than 3 mm wheal to commercial birch pollen extract.

Skin testing: Concentrations tested range from $10^{-3}$ μg/ml to 1 μg/ml (10-fold dilution series). An ID test result is considered positive when a wheal reaction superior to 5 mm (for birch pollen, Bet v 1 and peptides) in diameter and an erythema are present at a concentration ≤0.1 μg/ml.

Study design: The study is designed as a double blind, randomized, two-dose, placebo-controlled trial. At day 0, patients from the OPF group are injected at 30 min interval with successively 0.1 μg, 1 μg, 10 μg, 20 μg, 40 μg, 80 μg and 100 μg of each of the two OPFs. Patients are then injected at day 4, 7, 14, 42 and 70 with a maintenance dose of 100 μg of each of the two OPFs. A maintenance dose of 300 μg of each OPF is initially injected to two patients up to day 42. Patients from the control group are injected with an equivalent volume of peptide diluent only (0.3 mg/ml albumin solution, containing 4 mg/ml of phenol) (ALK/Abello, Horsholm, Denmark).

Peptide synthesis and purification: Two overlapping peptide fragments $OPF_{1-90}$ (SEQ ID NO:5) and $OPF_{80-160}$ (SEQ ID NO:6) mapping the entire 160 amino acids of Bet v 1 (SEQ ID NO: 7) are synthesized on an Applied Biosystems 431A Peptide Synthesizer (Perkin Elmer, Foster City, Calif.) and purified as described in Roggero et al., FEBS Lett. 408:285-288, 1997. Analytical HPLC and mass spectrometry are used to assess the purity of each peptide (>80%), which are readily soluble in PBS. On the day of injection, the peptide mixture is reconstituted in an 0.3 mg/ml albumin solution (containing 4 mg/ml of phenol) (ALK/Abello, Horsholm, Denmark) and injected subcutaneously in the deltoid area.

Reagents: Whole birch pollen and Bet v 1 is purchased. For cell culture, Bet v 1 is further purified by HPLC. Its cytotoxicity can be inhibited by overnight reduction at 37° C. with a 100 molar excess of dithiothreitol, followed by alkylation with a 1000 molar excess of N-ethylmaleimide. Bet v 1 is finally purified on a Sephadex G-25 column (Pharmacia, Uppsala, Sweden). PMA and ionomycin are purchased from Calbiochem, San Diego, Calif.

Proliferation assays: Blood is drawn immediately before each OPF injection and PBMC are isolated from heparinized blood by density gradient centrifugation over Ficoll-Paque (Pharmacia Biotech AB, Uppsala, Sweden). Prior to $^3$H-thymidine (Du Pont NEN Products Boston, Mass., USA) incorporation, PBMC ($2 \times 10^5$/well) from each donor is cultured for 6 days in octoplicates in 96 well flat bottom plates (Costar Corning Inc., New York, N.Y.) in RPMI 1640 medium (Gibco, Basel, Switzerland) containing 10% AB+ serum (Swiss Red Cross, Bern, Switzerland), 2 mM glutamine, 1% Na-pyruvate, 1% non-essential amino acids, 1% kanamycine (all from Gibco) with optimal concentration of OPFs (10 µg/ml) or Bet v 1 (10 µg/ml). See Kämmerer et al., J. Allergy Clin. Immunol. 100:96-103, 1997.

Short term T cell lines: T cell lines are derived from PBMC that is isolated before each injection and stimulated in 24 well plates (Nunc) ($10^6$ cells/well) with a mixture of the two OPFs (10 µg/ml) for 7 days in supplemented 10% AB+ RPMI 1640 medium as described above. The short term T cell lines obtained are washed and restimulated for 24 h (for IL-4, IL-5, IL-13 and TGFβ secretion) or 48 h (for IFNγ and IL-10) with plastic crosslinked OKT3 (1 µg/ml) (see Jutel et al., Clin. Experiment. Allergy 25:1108-1117, 1995). Cell culture supernatants are collected for cytokine quantification and stored at −80° C.

Cytokine quantification: IL-4, IL-10 and IFNγ are titrated using commercially available ELISA kits (Mabtech AG, Nacka, Sweden, for IL-4, IL-10 and IFNγ□□ and R&DSystem for IL-5, IL-13 and TGFβ), according to manufacturer's recommendations.

Quantification of specific serum IgE and $IgG_4$: Whole birch pollen and anti-Bet v 1 specific IgE will be quantified using the Phamarcia CAP System Fluoroimmunoassay (Pharmacia Diagnostic AB, Uppsala, Sweden) as described in Kämmerer et al., J. Allergy Clin. Immunol. 100:96-103, 1997. For quantification of specific anti-Bet v 1 IgG4, native Bet v 1 (5 µg/ml) is coated on 96 well plates (Maxisorb, Denmark) in carbonate/bicarbonate buffer pH 9.6, for 2 h at room temperature. Plates are blocked with milk 5%/PBS/Tween 0.05%. Serial dilutions of sera in 1% milk/Tween 0.05% are incubated for 1 h at room temperature. Plates are washed thrice, incubated with horseradish peroxidase labelled anti-IgG4 mAb JDC-14 $\frac{1}{10,000}$ (Pharmingen, Hamburg, Germany), and revealed in 3,3', 5,5'-tétraméthylbenzidine (TMB). Optical density is determined at 450 nm on a microtiter plate analyzer (MR5000, Dynatech Laboratories). Titers are reported to a standard serum and expressed as arbitrary standard units.

Immunoblotting and dot blot analysis: Anti-birch pollen or −Bet v1 immunoblots will be processed as described in Kettner et al., Clin. Experiment. Allergy 29:394-401, 1999. For dot blot analysis, 1 µg of whole birch pollen, Bet v 1, OPFs or human albumin will be diluted ¼ in DMSO, spotted on PVDF membranes and dried for 30 min. at 37° C. After blocking in non-fat milk 5%, further steps are performed as described in Kettner et al., Clin. Experiment. Allergy 29:394-401, 1999. Dot densities are analyzed by scanning densitometry using an Advanced American Biotechnology scanner, Fullerton, Calif.

Statistical analysis: Differences within and between groups are evaluated by non-parametric ANOVA tests (Friedman or Kruskal-Wallis non parametric test with multicomparison post-test, or Mann-Whitney test respectively); or by Fisher's exact test (between group differences: responders versus non-responders, positive responses being defined as a doubling of day 0 value), using an Instat 3.0 software.

Example 3

Birch Pollen Profilin (Bet v 2) Specific T Cell Tolerance Induction with Allergen-Derived Overlapping Peptide Fragments Materials and Methods Patients: Patients eligible for this study include those with a history of seasonal birch pollen allergy and with an SPT reaction 3-F compared with an albumin 10 mg/mL wheal and a minimal outcome of more than 3 mm wheal to commercial birch pollen extract.

Skin testing: Concentrations tested range from $10^{-3}$ µg/ml to 1 µg/ml (10-fold dilution series). An ID test result will be considered positive when a wheal reaction superior to 5 mm (for birch pollen profilin, Bet v 2 and peptides) in diameter and an erythema were present at a concentration ≤0.1 µg/ml.

Study design: The study is designed as a double blind, randomized, two-dose, placebo-controlled trial. At day 0, patients from the OPF group are injected at 30 min interval with successively 0.1 µg, 1 µg, 10 µg, 20 µg, 40 µg, 80 µg and 100 µg of each of the two OPFs. Patients are then injected at day 4, 7, 14, 42 and 70 with a maintenance dose of 100 µg of each of the two OPFs. A maintenance dose of 300 µg of each OPF is initially injected to two patients up to day 42. Patients from the control group are injected with an equivalent volume of peptide diluent only (0.3 mg/ml albumin solution, containing 4 mg/ml of phenol) (ALK/Abello, Horsholm, Denmark).

Peptide synthesis and purification: Two overlapping peptide fragments $OPF_{1-70}$ (SEQ ID NO:8) and $OPF_{60-133}$ (SEQ ID NO:9) mapping the entire 133 amino acids of Bet v 2 (SEQ ID NO: 10) are synthesized on an Applied Biosystems 431A Peptide Synthesizer (Perkin Elmer, Foster City, Calif.) and purified as described in Roggero et al., FEBS Lett. 408:285-288, 1997. Analytical HPLC and mass spectrometry are used to assess the purity of each peptide (>80%), which are readily soluble in PBS. On the day of injection, the peptide mixture is reconstituted in an 0.3 mg/ml albumin solution (containing 4 mg/ml of phenol) (ALK/Abello, Horsholm, Denmark) and injected subcutaneously in the deltoid area.

Reagents: Whole birch pollen profilin and Bet v 2 is purchased. For cell culture, Bet v 2 is further purified by HPLC. Its cytotoxicity can be inhibited by overnight reduction at 37° C. with a 100 molar excess of dithiothreitol, followed by alkylation with a 1000 molar excess of N-ethylmaleimide. Bet v 1 is finally purified on a Sephadex G-25 column (Pharmacia, Uppsala, Sweden). PMA and ionomycin are purchased from Calbiochem, San Diego, Calif.

Proliferation assays: Blood is drawn immediately before each OPF injection and PBMC are isolated from heparinized blood by density gradient centrifugation over Ficoll-Paque (Pharmacia Biotech AB, Uppsala, Sweden). Prior to $^3$H-thymidine (Du Pont NEN Products Boston, Mass., USA) incorporation, PBMC ($2 \times 10^5$/well) from each donor is cultured for 6 days in octoplicates in 96 well flat bottom plates (Costar Corning Inc., New York, N.Y.) in RPMI 1640 medium (Gibco, Basel, Switzerland) containing 10% AB+ serum (Swiss Red Cross, Bern, Switzerland), 2 mM glutamine, 1% Na-pyruvate, 1% non-essential amino acids, 1% kanamycine (all from Gibco) with optimal concentration of OPFs (10 µg/ml) or Bet v 1 (10 µg/ml). See Kämmerer et al., J. Allergy Clin. Immunol. 100:96-103, 1997.

Short term T cell lines: T cell lines are derived from PBMC that is isolated before each injection and stimulated in 24 well plates (Nunc) ($10^6$ cells/well) with a mixture of the two OPFs (10 μg/ml) for 7 days in supplemented 10% AB+RPMI 1640 medium as described above. The short term T cell lines obtained are washed and restimulated for 24 h (for IL-4, IL-5, IL-13 and TGFβ secretion) or 48 h (for IFNγ and IL-10) with plastic crosslinked OKT3 (1 μg/ml) (see Jutel et al., Clin. Experiment. Allergy 25:1108-1117, 1995). Cell culture supernatants are collected for cytokine quantification and stored at −80° C.

Cytokine quantification: IL-4, IL-10 and IFNγ are titrated using commercially available ELISA kits (Mabtech AG, Nacka, Sweden, for IL-4, IL-10 and IFNγ□□ and R&DSystem for IL-5, IL-13 and TGFβ), according to manufacturer's recommendations.

Quantification of specific serum IgE and $IgG_4$: Whole birch pollen profilin and anti-Bet v 2 specific IgE will be quantified using the Phamarcia CAP System Fluoroimmunoassay (Pharmacia Diagnostic AB, Uppsala, Sweden) as described in Kämmerer et al., J. Allergy Clin. Immunol. 100:96-103, 1997. For quantification of specific anti-Bet v 1 IgG4, native Bet v 2 (5 μg/ml) is coated on 96 well plates (Maxisorb, Denmark) in carbonate/bicarbonate buffer pH 9.6, for 2 h at room temperature. Plates are blocked with milk 5%/PBS/Tween 0.05%. Serial dilutions of sera in 1% milk/Tween 0.05% are incubated for 1 h at room temperature. Plates are washed thrice, incubated with horseradish peroxidase labelled anti-IgG4 mAb JDC-14 1/10,000 (Pharmingen, Hamburg, Germany), and revealed in 3,3', 5,5'-tétraméthylbenzidine (TMB). Optical density is determined at 450 nm on a microtiter plate analyzer (MR5000, Dynatech Laboratories). Titers are reported to a standard serum and expressed as arbitrary standard units.

Immunoblotting and dot blot analysis: Anti-birch pollen profilin or -Bet v 2 immunoblots will be processed as described in Kettner et al., Clin. Experiment. Allergy 29:394-401, 1999. For dot blot analysis, 1 μg of whole birch pollen profilin, Bet v 2, OPFs or human albumin will be diluted ¼ in DMSO, spotted on PVDF membranes and dried for 30 min. at 37° C. After blocking in non-fat milk 5%, further steps are performed as described in Kettner et al., Clin. Experiment. Allergy 29:394-401, 1999. Dot densities are analyzed by scanning densitometry using an Advanced American Biotechnology scanner, Fullerton, Calif.

Statistical analysis: Differences within and between groups are evaluated by non-parametric ANOVA tests (Friedman or Kruskal-Wallis non parametric test with multicomparison post-test, or Mann-Whitney test respectively); or by Fisher's exact test (between group differences: responders versus non-responders, positive responses being defined as a doubling of day 0 value), using an Instat 3.0 software.

Example 4

Dust Mite (Der p 1) Specific T Cell Tolerance Induction with Allergen-Derived Overlapping Peptide Fragments Materials and Methods Patients: Patients eligible for this study include those with a history of dust mite allergy and with an SPT reaction ≥3-F compared with an albumin 10 mg/mL wheal and a minimal outcome of more than 3 mm wheal to commercial dust mite extract.

Skin testing: Concentrations tested range from $10^{-3}$ μg/ml to 1 μg/ml (10-fold dilution series). An ID test result will be considered positive when a wheal reaction superior to 5 mm (for dust mite, Der p 1 and peptides) in diameter and an erythema were present at a concentration ≤0.1 μg/ml.

Study design: The study is designed as a double blind, randomized, two-dose, placebo-controlled trial. At day 0, patients from the OPF group are injected at 30 min interval with successively 0.1 μg, 1 μg, 10 μg, 20 μg, 40 μg, 80 μg and 100 μg of each of the two OPFs. Patients are then injected at day 4, 7, 14, 42 and 70 with a maintenance dose of 100 μg of each of the three OPFs. A maintenance dose of 300 μg of each OPF is initially injected to two patients up to day 42. Patients from the control group are injected with an equivalent volume of peptide diluent only (0.3 mg/ml albumin solution, containing 4 mg/ml of phenol) (ALK/Abello, Horsholm, Denmark).

Peptide synthesis and purification: Three overlapping peptide fragments $OPF_{1-81}$ (SEQ ID NO:11), $OPF_{67-152}$ (SEQ ID NO:12) and $OPF_{137-212}$ (SEQ ID NO:13) mapping the entire 212 amino acids of Der p 1 (SEQ ID NO: 14) are synthesized on an Applied Biosystems 431A Peptide Synthesizer (Perkin Elmer, Foster City, Calif.) and purified as described in Roggero et al., FEBS Lett. 408:285-288, 1997. Analytical HPLC and mass spectrometry are used to assess the purity of each peptide (>80%), which are readily soluble in PBS. On the day of injection, the peptide mixture is reconstituted in an 0.3 mg/ml albumin solution (containing 4 mg/ml of phenol) (ALK/Abello, Horsholm, Denmark) and injected subcutaneously in the deltoid area.

Reagents: Whole DM and Der p 1 is purchased. For cell culture, Der p 1 is further purified by HPLC. Its cytotoxicity can be inhibited by overnight reduction at 37° C. with a 100 molar excess of dithiothreitol, followed by alkylation with a 1000 molar excess of N-ethylmaleimide. Der p 1 is finally purified on a Sephadex G-25 column (Pharmacia, Uppsala, Sweden). PMA and ionomycin are purchased from Calbiochem, San Diego, Calif.

Proliferation assays: Blood is drawn immediately before each OPF injection and PBMC are isolated from heparinized blood by density gradient centrifugation over Ficoll-Paque (Pharmacia Biotech AB, Uppsala, Sweden). Prior to $^3$H-thymidine (Du Pont NEN Products Boston, Mass., USA) incorporation, PBMC ($2\times10^5$/well) from each donor is cultured for 6 days in octoplicates in 96 well flat bottom plates (Costar Corning Inc., New York, N.Y.) in RPMI 1640 medium (Gibco, Basel, Switzerland) containing 10% $AB^+$ serum (Swiss Red Cross, Bern, Switzerland), 2 mM glutamine, 1% Na-pyruvate, 1% non-essential amino acids, 1% kanamycine (all from Gibco) with optimal concentration of OPFs (10 μg/ml) or Bet v 1 (10 μg/ml). See Kämmerer et al., J. Allergy Clin. Immunol. 100:96-103, 1997.

Short term T cell lines: T cell lines are derived from PBMC that is isolated before each injection and stimulated in 24 well plates (Nunc) ($10^6$ cells/well) with a mixture of the three OPFs (10 μg/ml) for 7 days in supplemented 10% AB+RPMI 1640 medium as described above. The short term T cell lines obtained are washed and restimulated for 24 h (for IL-4, IL-5, IL-13 and TGFβ secretion) or 48 h (for IFNγ and IL-10) with plastic crosslinked OKT3 (1 μg/ml) (see Jutel et al., Clin. Experiment. Allergy 25:1108-1117, 1995). Cell culture supernatants are collected for cytokine quantification and stored at −80° C.

Cytokine quantification: IL-4, IL-10 and IFNγ are titrated using commercially available ELISA kits (Mabtech AG, Nacka, Sweden, for IL-4, IL-10 and IFNγ□□ and R&DSystem for IL-5, IL-13 and TGFβ), according to manufacturer's recommendations.

Quantification of specific serum IgE and $IgG_4$: Whole DM and anti-Der p 1 specific IgE will be quantified using the Phamarcia CAP System Fluoroimmunoassay (Pharmacia Diagnostic AB, Uppsala, Sweden) as described in Kämmerer et al., J. Allergy Clin. Immunol. 100:96-103, 1997. For quantification of specific anti-Der p 1 IgG4, native Der p 1 (5 µg/ml) is coated on 96 well plates (Maxisorb, Denmark) in carbonate/bicarbonate buffer pH 9.6, for 2 h at room temperature. Plates are blocked with milk 5%/PBS/Tween 0.05%. Serial dilutions of sera in 1% milk/Tween 0.05% are incubated for 1 h at room temperature. Plates are washed thrice, incubated with horseradish peroxidase labelled anti-IgG4 mAb JDC-14 $1/10,000$ (Pharmingen, Hamburg, Germany), and revealed in 3,3', 5,5'-tétraméthylbenzidine (TMB). Optical density is determined at 450 nm on a microtiter plate analyzer (MR5000, Dynatech Laboratories). Titers are reported to a standard serum and expressed as arbitrary standard units.

Immunoblotting and dot blot analysis: Anti-DM or -Der p 1 immunoblots will be processed as described in Kettner et al., Clin. Experiment. Allergy 29:394-401, 1999. For dot blot analysis, 1 µg of dust mite allergen, Der p 1, OPFs or human albumin will be diluted ¼ in DMSO, spotted on PVDF membranes and dried for 30 min. at 37° C. After blocking in non-fat milk 5%, further steps are performed as described in Kettner et al., Clin. Experiment. Allergy 29:394-401, 1999. Dot densities are analyzed by scanning densitometry using an Advanced American Biotechnology scanner, Fullerton, Calif.

Statistical analysis: Differences within and between groups are evaluated by non-parametric ANOVA tests (Friedman or Kruskal-Wallis non parametric test with multicomparison post-test, or Mann-Whitney test respectively); or by Fisher's exact test (between group differences: responders versus non-responders, positive responses being defined as a doubling of day 0 value), using an Instat 3.0 software.

Example 5

Dust Mite (Der p 2) Specific T Cell Tolerance Induction with Allergen-Derived Overlapping Peptide Fragments Materials and Methods Patients: Patients eligible for this study include those with a history of dust mite allergy and with an SPT reaction 3-F compared with an albumin 10 mg/mL wheal and a minimal outcome of more than 3 mm wheal to commercial dust mite extract.

Skin testing: Concentrations tested range from $10^{-3}$ µg/ml to 1 µg/ml (10-fold dilution series). An ID test result will be considered positive when a wheal reaction superior to 5 mm (for dust mite, Der p 2 and peptides) in diameter and an erythema were present at a concentration ≤0.1 µg/ml.

Study design: The study is designed as a double blind, randomized, two-dose, placebo-controlled trial. At day 0, patients from the OPF group are injected at 30 min interval with successively 0.1 µg, 1 µg, 10 µg, 20 µg, 40 µg, 80 µg and 100 µg of each of the two OPFs. Patients are then injected at day 4, 7, 14, 42 and 70 with a maintenance dose of 100 µg of each of the three OPFs. A maintenance dose of 300 µg of each OPF is initially injected to two patients up to day 42. Patients from the control group are injected with an equivalent volume of peptide diluent only (0.3 mg/ml albumin solution, containing 4 mg/ml of phenol) (ALK/Abello, Horsholm, Denmark).

Peptide synthesis and purification: Two overlapping peptide fragments $OPF_{1-73}$ (SEQ ID NO:15) and $OPF_{57-136}$ (SEQ ID NO:16) mapping the entire 136 amino acids of Der p 2 (SEQ ID NO: 17) are synthesized on an Applied Biosystems 431A Peptide Synthesizer (Perkin Elmer, Foster City, Calif.) and purified as described in Roggero et al., FEBS Lett. 408:285-288, 1997. Analytical HPLC and mass spectrometry are used to assess the purity of each peptide (>80%), which are readily soluble in PBS. On the day of injection, the peptide mixture is reconstituted in an 0.3 mg/ml albumin solution (containing 4 mg/ml of phenol) (ALK/Abello, Horsholm, Denmark) and injected subcutaneously in the deltoid area.

Reagents: Whole DM and Der p 2 is purchased. For cell culture, Der p 2 is further purified by HPLC. Its cytotoxicity can be inhibited by overnight reduction at 37° C. with a 100 molar excess of dithiothreitol, followed by alkylation with a 1000 molar excess of N-ethylmaleimide. Der p 2 is finally purified on a Sephadex G-25 column (Pharmacia, Uppsala, Sweden). PMA and ionomycin are purchased from Calbiochem, San Diego, Calif.

Proliferation assays: Blood is drawn immediately before each OPF injection and PBMC are isolated from heparinized blood by density gradient centrifugation over Ficoll-Paque (Pharmacia Biotech AB, Uppsala, Sweden). Prior to $^3$H-thymidine (Du Pont NEN Products Boston, Mass., USA) incorporation, PBMC ($2 \times 10^5$/well) from each donor is cultured for 6 days in octoplicates in 96 well flat bottom plates (Costar Corning Inc., New York, N.Y.) in RPMI 1640 medium (Gibco, Basel, Switzerland) containing 10% AB$^+$ serum (Swiss Red Cross, Bern, Switzerland), 2 mM glutamine, 1% Na-pyruvate, 1% non-essential amino acids, 1% kanamycine (all from Gibco) with optimal concentration of OPFs (10 µg/ml) or Bet v 1 (10 µg/ml). See Kämmerer et al., J. Allergy Clin. Immunol. 100:96-103, 1997.

Short term T cell lines: T cell lines are derived from PBMC that is isolated before each injection and stimulated in 24 well plates (Nunc) ($10^6$ cells/well) with a mixture of the two OPFs (10 µg/ml) for 7 days in supplemented 10% AB+RPMI 1640 medium as described above. The short term T cell lines obtained are washed and restimulated for 24 h (for IL-4, IL-5, IL-13 and TGFβ secretion) or 48 h (for IFNγ and IL-10) with plastic crosslinked OKT3 (1 µg/ml) (see Jutel et al., Clin. Experiment. Allergy 25:1108-1117, 1995). Cell culture supernatants are collected for cytokine quantification and stored at −80° C.

Cytokine quantification: IL-4, IL-10 and IFNγ are titrated using commercially available ELISA kits (Mabtech AG, Nacka, Sweden, for IL-4, IL-10 and IFNγ□□ and R&DSystem for IL-5, IL-13 and TGFβ), according to manufacturer's recommendations.

Quantification of specific serum IgE and IgG$_4$: Whole DM and anti-Der p 2 specific IgE will be quantified using the Phamarcia CAP System Fluoroimmunoassay (Pharmacia Diagnostic AB, Uppsala, Sweden) as described in Kämmerer et al., J. Allergy Clin. Immunol. 100:96-103, 1997. For quantification of specific anti-Der p 2 IgG4, native Der p 2 (5 µg/ml) is coated on 96 well plates (Maxisorb, Denmark) in carbonate/bicarbonate buffer pH 9.6, for 2 h at room temperature. Plates are blocked with milk 5%/PBS/Tween 0.05%. Serial dilutions of sera in 1% milk/Tween 0.05% are incubated for 1 h at room temperature. Plates are washed thrice, incubated with horseradish peroxidase labelled anti-IgG4 mAb JDC-14 $1/10,000$ (Pharmingen, Hamburg, Germany), and revealed in 3,3', 5,5'-tétraméthylbenzidine (TMB). Optical density is determined at 450 nm on a microtiter plate analyzer (MR5000, Dynatech Laboratories). Titers are reported to a standard serum and expressed as arbitrary standard units.

Immunoblotting and dot blot analysis: Anti-DM or -Der p 2 immunoblots will be processed as described in Kettner et al., Clin. Experiment. Allergy 29:394-401, 1999. For dot blot analysis, 1 µg of dust mite allergen, Der p 2, OPFs or human albumin will be diluted ¼ in DMSO, spotted on PVDF membranes and dried for 30 min. at 37° C. After blocking in non-fat milk 5%, further steps are performed as described in Kettner et al., Clin. Experiment. Allergy 29:394-401, 1999. Dot densities are analyzed by scanning densitometry using an Advanced American Biotechnology scanner, Fullerton, Calif.

Statistical analysis: Differences within and between groups are evaluated by non-parametric ANOVA tests (Friedman or Kruskal-Wallis non parametric test with multicomparison post-test, or Mann-Whitney test respectively); or by Fisher's exact test (between group differences: responders versus non-responders, positive responses being defined as a doubling of day 0 value), using an Instat 3.0 software.

Other Embodiments

From the foregoing detailed description of the specific embodiments of the invention, it should be apparent that unique methods and compositions have been described. Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims.

What is claimed is:

1. A composition comprising a plurality of contiguous overlapping peptide fragments 30 to 73 amino acids in length which peptide fragments consist of peptides within SEQ ID NOs: 8 and 9 which together comprise the entire amino acid sequence of a birch pollen profilin allergen (SEQ ID NO: 10), wherein said fragments are capable of inducing a T cell response in patients hypersensitive to said allergen wherein the reactivity of said peptides to IgE antibodies of subjects who are allergic to birch pollen profilin allergen is significantly reduced or eliminated while the reactivity with the T lymphocytes from subjects who are allergic to birch pollen profilin allergen is retained.

* * * * *

SEQUENCE LISTING

```
<160> NUMBER OF SEQ ID NOS: 23

<210> SEQ ID NO 1
<211> LENGTH: 60
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1

Ile Ile Tyr Pro Gly Thr Leu Trp Cys Gly His Gly Asn Lys Ser Ser
1               5                   10                  15

Gly Pro Asn Glu Leu Gly Arg Phe Lys His Thr Asp Ala Cys Cys Arg
            20                  25                  30

Thr His Asp Met Cys Pro Asp Val Met Ser Ala Gly Glu Ser Lys His
        35                  40                  45

Gly Leu Thr Asn Thr Ala Ser His Thr Arg Leu Ser
    50                  55                  60

<210> SEQ ID NO 2
<211> LENGTH: 53
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Lys His Gly Leu Thr Asn Thr Ala Ser His Thr Arg Leu Ser Cys Asp
1               5                   10                  15

Cys Asp Asp Lys Phe Tyr Asp Cys Leu Lys Asn Ser Ala Asp Thr Ile
            20                  25                  30

Ser Ser Tyr Phe Val Gly Lys Met Tyr Phe Asn Leu Ile Asp Thr Lys
        35                  40                  45

Cys Tyr Lys Leu Glu
    50

<210> SEQ ID NO 3
<211> LENGTH: 45
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 3

Leu Ile Asp Thr Lys Cys Tyr Lys Leu Glu His Pro Val Thr Gly Cys
1               5                   10                  15

Gly Glu Arg Thr Glu Gly Arg Cys Leu His Tyr Thr Val Asp Lys Ser
            20                  25                  30

Lys Pro Lys Val Tyr Gln Trp Phe Asp Leu Arg Lys Tyr
        35                  40                  45

<210> SEQ ID NO 4
<211> LENGTH: 134
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Ile Ile Tyr Pro Gly Thr Leu Trp Cys Gly His Gly Asn Lys Ser Ser
1               5                   10                  15

Gly Pro Asn Glu Leu Gly Arg Phe Lys His Thr Asp Ala Cys Cys Arg
            20                  25                  30

Thr His Asp Met Cys Pro Asp Val Met Ser Ala Gly Glu Ser Lys His
            35                  40                  45

Gly Leu Thr Asn Thr Ala Ser His Thr Arg Leu Ser Cys Asp Cys Asp
50                  55                  60

Asp Lys Phe Tyr Asp Cys Leu Lys Asn Ser Ala Asp Thr Ile Ser Ser
65                  70                  75                  80

Tyr Phe Val Gly Lys Met Tyr Phe Asn Leu Ile Asp Thr Lys Cys Tyr
                85                  90                  95

Lys Leu Glu His Pro Val Thr Gly Cys Gly Glu Arg Thr Glu Gly Arg
            100                 105                 110

Cys Leu His Tyr Thr Val Asp Lys Ser Lys Pro Lys Val Tyr Gln Trp
        115                 120                 125

Phe Asp Leu Arg Lys Tyr
        130

<210> SEQ ID NO 5
<211> LENGTH: 90
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Met Gly Val Phe Asn Tyr Glu Thr Glu Ala Thr Ser Val Ile Pro Ala
1               5                   10                  15

Ala Arg Leu Phe Lys Ala Phe Ile Leu Asp Gly Asp Asn Leu Phe Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Ser Phe Pro Glu Gly Phe Pro
50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly
                85                  90
```

```
<210> SEQ ID NO 6
<211> LENGTH: 80
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Lys Tyr Asn Tyr Ser Val Ile Glu Gly Gly Pro Ile Gly Asp Thr Leu
1               5                   10                  15

Glu Lys Ile Ser Asn Glu Ile Lys Ile Val Ala Thr Pro Asp Gly Gly
            20                  25                  30

Ser Ile Leu Lys Ile Ser Asn Lys Tyr His Thr Lys Gly Asp His Glu
        35                  40                  45

Val Lys Ala Glu Gln Val Lys Ala Ser Lys Glu Met Gly Glu Thr Leu
    50                  55                  60

Leu Arg Ala Val Glu Ser Tyr Leu Leu Ala His Ser Asp Ala Tyr Asn
65                  70                  75                  80

<210> SEQ ID NO 7
<211> LENGTH: 160
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Met Gly Val Phe Asn Tyr Glu Thr Glu Ala Thr Ser Val Ile Pro Ala
1               5                   10                  15

Ala Arg Leu Phe Lys Ala Phe Ile Leu Asp Gly Asp Asn Leu Phe Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Ser Phe Pro Glu Gly Phe Pro
    50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Ile Gly Asp Thr Leu
                85                  90                  95

Glu Lys Ile Ser Asn Glu Ile Lys Ile Val Ala Thr Pro Asp Gly Gly
            100                 105                 110

Ser Ile Leu Lys Ile Ser Asn Lys Tyr His Thr Lys Gly Asp His Glu
        115                 120                 125

Val Lys Ala Glu Gln Val Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160

<210> SEQ ID NO 8
<211> LENGTH: 70
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Met Ser Trp Gln Thr Tyr Val Asp Glu His Leu Met Ser Asp Ile Asp
1               5                   10                  15
```

Gly Gln Ala Ser Asn Ser Leu Ala Ser Ala Ile Val Gly His Asp Gly
            20                  25                  30

Ser Val Trp Ala Gln Ser Ser Ser Phe Pro Gln Phe Lys Pro Gln Glu
        35                  40                  45

Ile Thr Gly Ile Met Lys Asp Phe Glu Glu Pro Gly His Leu Ala Pro
    50                  55                  60

Thr Gly Leu His Leu Gly
65              70

<210> SEQ ID NO 9
<211> LENGTH: 73
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

His Leu Ala Pro Thr Gly Leu His Leu Gly Gly Ile Lys Tyr Met Val
1               5                   10                  15

Ile Gln Gly Glu Ala Gly Ala Val Ile Arg Gly Lys Lys Gly Ser Gly
            20                  25                  30

Gly Ile Thr Ile Lys Lys Thr Gly Gln Ala Leu Val Phe Gly Ile Tyr
        35                  40                  45

Glu Glu Pro Val Thr Pro Gly Gln Ser Asn Met Val Val Glu Arg Leu
    50                  55                  60

Gly Asp Tyr Leu Ile Asp Gln Gly Leu
65                  70

<210> SEQ ID NO 10
<211> LENGTH: 133
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

Met Ser Trp Gln Thr Tyr Val Asp Glu His Leu Met Ser Asp Ile Asp
1               5                   10                  15

Gly Gln Ala Ser Asn Ser Leu Ala Ser Ala Ile Val Gly His Asp Gly
            20                  25                  30

Ser Val Trp Ala Gln Ser Ser Ser Phe Pro Gln Phe Lys Pro Gln Glu
        35                  40                  45

Ile Thr Gly Ile Met Lys Asp Phe Glu Glu Pro Gly His Leu Ala Pro
    50                  55                  60

Thr Gly Leu His Leu Gly Gly Ile Lys Tyr Met Val Ile Gln Gly Glu
65                  70                  75                  80

Ala Gly Ala Val Ile Arg Gly Lys Lys Gly Ser Gly Gly Ile Thr Ile
                85                  90                  95

Lys Lys Thr Gly Gln Ala Leu Val Phe Gly Ile Tyr Glu Glu Pro Val
            100                 105                 110

Thr Pro Gly Gln Ser Asn Met Val Val Glu Arg Leu Gly Asp Tyr Leu
        115                 120                 125

Ile Asp Gln Gly Leu
    130

<210> SEQ ID NO 11

```
<211> LENGTH: 81
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Thr Asn Ala Cys Ser Ile Asn Gly Asn Ala Pro Ala Glu Ile Asp Leu
1               5                   10                  15

Arg Gln Met Arg Thr Val Thr Pro Ile Arg Met Gln Gly Gly Cys Gly
            20                  25                  30

Ser Cys Trp Ala Phe Ser Gly Val Ala Ala Thr Glu Ser Ala Tyr Leu
        35                  40                  45

Ala Tyr Arg Asn Gln Ser Leu Asp Leu Ala Glu Gln Glu Leu Val Asp
    50                  55                  60

Cys Ala Ser Gln His Gly Cys His Gly Asp Thr Ile Pro Arg Gly Ile
65                  70                  75                  80

Glu

<210> SEQ ID NO 12
<211> LENGTH: 86
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Ser Gln His Gly Cys His Gly Asp Thr Ile Pro Arg Gly Ile Glu Tyr
1               5                   10                  15

Ile Gln His Asn Gly Val Val Gln Glu Ser Tyr Tyr Arg Tyr Val Ala
            20                  25                  30

Arg Glu Gln Ser Cys Arg Arg Pro Asn Ala Gln Arg Phe Gly Ile Ser
        35                  40                  45

Asn Tyr Cys Gln Ile Tyr Pro Pro Asn Val Asn Lys Ile Arg Glu Ala
    50                  55                  60

Leu Ala Gln Thr His Ser Ala Ile Ala Val Ile Ile Gly Ile Lys Asp
65                  70                  75                  80

Leu Asp Ala Phe Arg His
                85

<210> SEQ ID NO 13
<211> LENGTH: 86
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

Ala Ile Ala Val Ile Ile Gly Ile Lys Asp Leu Asp Ala Phe Arg His
1               5                   10                  15

Tyr Asp Gly Arg Thr Ile Ile Gln Arg Asp Asn Gly Tyr Gln Pro Asn
            20                  25                  30

Tyr His Ala Val Asn Ile Val Gly Tyr Ser Asn Ala Gln Gly Val Asp
        35                  40                  45

Tyr Trp Ile Val Arg Asn Ser Trp Asp Thr Asn Trp Gly Asp Asn Gly
    50                  55                  60

Tyr Gly Tyr Phe Ala Ala Asn Ile Asp Leu Met Met Ile Glu Glu Tyr
```

```
65                  70                  75                  80

Pro Tyr Val Val Ile Leu
                85

<210> SEQ ID NO 14
<211> LENGTH: 222
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 14

Thr Asn Ala Cys Ser Ile Asn Gly Asn Ala Pro Ala Glu Ile Asp Leu
1               5                   10                  15

Arg Gln Met Arg Thr Val Thr Pro Ile Arg Met Gln Gly Gly Cys Gly
            20                  25                  30

Ser Cys Trp Ala Phe Ser Gly Val Ala Ala Thr Glu Ser Ala Tyr Leu
        35                  40                  45

Ala Tyr Arg Asn Gln Ser Leu Asp Leu Ala Glu Gln Glu Leu Val Asp
    50                  55                  60

Cys Ala Ser Gln His Gly Cys His Gly Asp Thr Ile Pro Arg Gly Ile
65                  70                  75                  80

Glu Tyr Ile Gln His Asn Gly Val Val Gln Glu Ser Tyr Tyr Arg Tyr
                85                  90                  95

Val Ala Arg Glu Gln Ser Cys Arg Arg Pro Asn Ala Gln Arg Phe Gly
            100                 105                 110

Ile Ser Asn Tyr Cys Gln Ile Tyr Pro Pro Asn Val Asn Lys Ile Arg
        115                 120                 125

Glu Ala Leu Ala Gln Thr His Ser Ala Ile Ala Val Ile Ile Gly Ile
    130                 135                 140

Lys Asp Leu Asp Ala Phe Arg His Tyr Asp Gly Arg Thr Ile Ile Gln
145                 150                 155                 160

Arg Asp Asn Gly Tyr Gln Pro Asn Tyr His Ala Val Asn Ile Val Gly
                165                 170                 175

Tyr Ser Asn Ala Gln Gly Val Asp Tyr Trp Ile Val Arg Asn Ser Trp
            180                 185                 190

Asp Thr Asn Trp Gly Asp Asn Gly Tyr Gly Tyr Phe Ala Ala Asn Ile
        195                 200                 205

Asp Leu Met Met Ile Glu Glu Tyr Pro Tyr Val Val Ile Leu
    210                 215                 220

<210> SEQ ID NO 15
<211> LENGTH: 72
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 15

Asp Gln Val Asp Val Lys Asp Cys Ala Asn His Glu Ile Lys Lys Val
1               5                   10                  15

Leu Val Pro Gly Cys His Gly Ser Glu Pro Cys Ile Ile His Arg Gly
            20                  25                  30

Lys Pro Phe Gln Leu Glu Ala Val Phe Glu Ala Asn Gln Asn Thr Lys
        35                  40                  45

Thr Ala Lys Ile Glu Ile Lys Ala Ser Ile Asp Gly Leu Glu Val Asp
```

```
                50                  55                  60
Val Pro Gly Ile Asp Pro Asn Ala
 65                  70

<210> SEQ ID NO 16
<211> LENGTH: 73
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 16

Ser Ile Asp Gly Leu Glu Val Asp Val Pro Gly Ile Asp Pro Asn Ala
 1               5                  10                  15

Cys His Tyr Met Lys Cys Pro Leu Val Lys Gly Gln Gln Tyr Asp Ile
                20                  25                  30

Lys Tyr Thr Trp Asn Val Pro Lys Ile Ala Pro Lys Ser Glu Asn Val
             35                  40                  45

Val Val Thr Val Lys Val Met Gly Asp Asp Gly Val Leu Ala Cys Ala
         50                  55                  60

Ile Ala Thr His Ala Lys Ile Arg Asp
 65                  70

<210> SEQ ID NO 17
<211> LENGTH: 136
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 17

Leu Val Ala Ala Val Ala Arg Asp Gln Val Asp Val Lys Asp Cys Ala
 1               5                  10                  15

Asn His Glu Ile Lys Lys Val Leu Val Pro Gly Cys His Gly Ser Glu
                20                  25                  30

Pro Cys Ile Ile His Arg Gly Lys Pro Phe Gln Leu Glu Ala Val Phe
             35                  40                  45

Glu Ala Asn Gln Asn Thr Lys Thr Ala Lys Ile Glu Ile Lys Ala Ser
         50                  55                  60

Ile Asp Gly Leu Glu Val Asp Val Pro Gly Ile Asp Pro Asn Ala Cys
 65                  70                  75                  80

His Tyr Met Lys Cys Pro Leu Val Lys Gly Gln Gln Tyr Asp Ile Lys
                85                  90                  95

Tyr Thr Trp Asn Val Pro Lys Ile Ala Pro Lys Ser Glu Asn Val Val
            100                 105                 110

Val Thr Val Lys Val Met Gly Asp Asp Gly Val Leu Ala Cys Ala Ile
        115                 120                 125

Ala Thr His Ala Lys Ile Arg Asp
            130                 135

<210> SEQ ID NO 18
<211> LENGTH: 160
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 18
```

```
Met Gly Val Phe Asn Tyr Glu Thr Glu Ala Thr Ser Val Ile Pro Ala
1               5                   10                  15

Ala Arg Leu Phe Lys Ala Phe Ile Leu Asp Gly Asp Asn Leu Phe Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Ser Phe Pro Glu Gly Phe Pro
    50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Met Ser Trp Gln Thr Tyr
                85                  90                  95

Val Asp Glu His Leu Met Ser Asp Ile Asp Gly Gln Ala Ser Asn Ser
            100                 105                 110

Leu Ala Ser Ala Ile Val Gly His Asp Gly Ser Val Trp Ala Gln Ser
        115                 120                 125

Ser Ser Phe Pro Gln Phe Lys Pro Gln Glu Ile Thr Gly Ile Met Lys
    130                 135                 140

Asp Phe Glu Glu Pro Gly His Leu Ala Pro Thr Gly Leu His Leu Gly
145                 150                 155                 160

<210> SEQ ID NO 19
<211> LENGTH: 153
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

His Leu Ala Pro Thr Gly Leu His Leu Gly Gly Ile Lys Tyr Met Val
1               5                   10                  15

Ile Gln Gly Glu Ala Gly Ala Val Ile Arg Gly Lys Lys Gly Ser Gly
            20                  25                  30

Gly Ile Thr Ile Lys Lys Thr Gly Gln Ala Leu Val Phe Gly Ile Tyr
        35                  40                  45

Glu Glu Pro Val Thr Pro Gly Gln Ser Asn Met Val Val Glu Arg Leu
    50                  55                  60

Gly Asp Tyr Leu Ile Asp Gln Gly Leu Lys Tyr Asn Tyr Ser Val Ile
65                  70                  75                  80

Glu Gly Gly Pro Ile Gly Asp Thr Leu Glu Lys Ile Ser Asn Glu Ile
                85                  90                  95

Lys Ile Val Ala Thr Pro Asp Gly Gly Ser Ile Leu Lys Ile Ser Asn
            100                 105                 110

Lys Tyr His Thr Lys Gly Asp His Glu Val Lys Ala Glu Gln Val Lys
        115                 120                 125

Ala Ser Lys Glu Met Gly Glu Thr Leu Leu Arg Ala Val Glu Ser Tyr
    130                 135                 140

Leu Leu Ala His Ser Asp Ala Tyr Asn
145                 150

<210> SEQ ID NO 20
<211> LENGTH: 160
<212> TYPE: PRT
<213> ORGANISM: Artificial Sequence
<220> FEATURE:
<223> OTHER INFORMATION: Description of Artificial Sequence: Synthetic
```

-continued

Peptide

<400> SEQUENCE: 20

Met Ser Trp Gln Thr Tyr Val Asp Glu His Leu Met Ser Asp Ile Asp
1               5                   10                  15

Gly Gln Ala Ser Asn Ser Leu Ala Ser Ala Ile Val Gly His Asp Gly
            20                  25                  30

Ser Val Trp Ala Gln Ser Ser Ser Phe Pro Gln Phe Lys Pro Gln Glu
        35                  40                  45

Ile Thr Gly Ile Met Lys Asp Phe Glu Glu Pro Gly His Leu Ala Pro
    50                  55                  60

Thr Gly Leu His Leu Gly Met Gly Val Phe Asn Tyr Glu Thr Glu Ala
65                  70                  75                  80

Thr Ser Val Ile Pro Ala Ala Arg Leu Phe Lys Ala Phe Ile Leu Asp
                85                  90                  95

Gly Asp Asn Leu Phe Pro Lys Val Ala Pro Gln Ala Ile Ser Ser Val
            100                 105                 110

Glu Asn Ile Glu Gly Asn Gly Gly Pro Gly Thr Ile Lys Lys Ile Ser
        115                 120                 125

Phe Pro Glu Gly Phe Pro Phe Lys Tyr Val Lys Asp Arg Val Asp Glu
    130                 135                 140

Val Asp His Thr Asn Phe Lys Tyr Asn Tyr Ser Val Ile Glu Gly Gly
145                 150                 155                 160

<210> SEQ ID NO 21
<211> LENGTH: 153
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 21

Lys Tyr Asn Tyr Ser Val Ile Glu Gly Gly Pro Ile Gly Asp Thr Leu
1               5                   10                  15

Glu Lys Ile Ser Asn Glu Ile Lys Ile Val Ala Thr Pro Asp Gly Gly
            20                  25                  30

Ser Ile Leu Lys Ile Ser Asn Lys Tyr His Thr Lys Gly Asp His Glu
        35                  40                  45

Val Lys Ala Glu Gln Val Lys Ala Ser Lys Glu Met Gly Glu Thr Leu
    50                  55                  60

Leu Arg Ala Val Glu Ser Tyr Leu Leu Ala His Ser Asp Ala Tyr Asn
65                  70                  75                  80

His Leu Ala Pro Thr Gly Leu His Leu Gly Gly Ile Lys Tyr Met Val
                85                  90                  95

Ile Gln Gly Glu Ala Gly Ala Val Ile Arg Gly Lys Lys Gly Ser Gly
            100                 105                 110

Gly Ile Thr Ile Lys Lys Thr Gly Gln Ala Leu Val Phe Gly Ile Tyr
        115                 120                 125

Glu Glu Pro Val Thr Pro Gly Gln Ser Asn Met Val Val Glu Arg Leu
    130                 135                 140

Gly Asp Tyr Leu Ile Asp Gln Gly Leu
145                 150

<210> SEQ ID NO 22
<211> LENGTH: 153
<212> TYPE: PRT

```
<213> ORGANISM: Artificial Sequence
<220> FEATURE:
<223> OTHER INFORMATION: Description of Artificial Sequence: Synthetic
      Peptide

<400> SEQUENCE: 22

Asp Gln Val Asp Val Lys Asp Cys Ala Asn His Glu Ile Lys Lys Val
1               5                   10                  15

Leu Val Pro Gly Cys His Gly Ser Glu Pro Cys Ile Ile His Arg Gly
            20                  25                  30

Lys Pro Phe Gln Leu Glu Ala Val Phe Glu Ala Asn Gln Asn Thr Lys
        35                  40                  45

Thr Ala Lys Ile Glu Ile Lys Ala Ser Ile Asp Gly Leu Glu Val Asp
    50                  55                  60

Val Pro Gly Ile Asp Pro Asn Ala Thr Asn Ala Cys Ser Ile Asn Gly
65                  70                  75                  80

Asn Ala Pro Ala Glu Ile Asp Leu Arg Gln Met Arg Thr Val Thr Pro
                85                  90                  95

Ile Arg Met Gln Gly Gly Cys Gly Ser Cys Trp Ala Phe Ser Gly Val
            100                 105                 110

Ala Ala Thr Glu Ser Ala Tyr Leu Ala Tyr Arg Asn Gln Ser Leu Asp
        115                 120                 125

Leu Ala Glu Gln Glu Leu Val Asp Cys Ala Ser Gln His Gly Cys His
    130                 135                 140

Gly Asp Thr Ile Pro Arg Gly Ile Glu
145                 150

<210> SEQ ID NO 23
<211> LENGTH: 159
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 23

Ala Ile Ala Val Ile Ile Gly Ile Lys Asp Leu Asp Ala Phe Arg His
1               5                   10                  15

Tyr Asp Gly Arg Thr Ile Ile Gln Arg Asp Asn Gly Tyr Gln Pro Asn
            20                  25                  30

Tyr His Ala Val Asn Ile Val Gly Tyr Ser Asn Ala Gln Gly Val Asp
        35                  40                  45

Tyr Trp Ile Val Arg Asn Ser Trp Asp Thr Asn Trp Gly Asp Asn Gly
    50                  55                  60

Tyr Gly Tyr Phe Ala Ala Asn Ile Asp Leu Met Met Ile Glu Glu Tyr
65                  70                  75                  80

Pro Tyr Val Val Ile Leu Ser Ile Asp Gly Leu Glu Val Asp Val Pro
                85                  90                  95

Gly Ile Asp Pro Asn Ala Cys His Tyr Met Lys Cys Pro Leu Val Lys
            100                 105                 110

Gly Gln Gln Tyr Asp Ile Lys Tyr Thr Trp Asn Val Pro Lys Ile Ala
        115                 120                 125

Pro Lys Ser Glu Asn Val Val Val Thr Val Lys Val Met Gly Asp Asp
    130                 135                 140

Gly Val Leu Ala Cys Ala Ile Ala Thr His Ala Lys Ile Arg Asp
145                 150                 155
```